United States Patent
Imfeld et al.

(10) Patent No.: US 12,329,528 B2
(45) Date of Patent: Jun. 17, 2025

(54) PROBE ARRAYS

(71) Applicant: 3Brain AG, Pfäffikon (CH)

(72) Inventors: Kilian Imfeld, Wädenswil (CH); Mauro Gandolfo, Zurich (CH); Alessandro Maccione, Genoa (IT)

(73) Assignee: 3Brain AG, Pfäffikon (CH)

( * ) Notice: Subject to any disclaimer, the term of this patent is extended or adjusted under 35 U.S.C. 154(b) by 493 days.

(21) Appl. No.: 17/618,249

(22) PCT Filed: Jun. 10, 2020

(86) PCT No.: PCT/EP2020/066125
§ 371 (c)(1),
(2) Date: Dec. 10, 2021

(87) PCT Pub. No.: WO2020/249634
PCT Pub. Date: Dec. 17, 2020

(65) Prior Publication Data
US 2022/0296149 A1    Sep. 22, 2022

(30) Foreign Application Priority Data

Jun. 11, 2019  (GB) ...................................... 1908326

(51) Int. Cl.
*A61B 5/30* (2021.01)
*A61B 5/00* (2006.01)
*A61N 1/04* (2006.01)

(52) U.S. Cl.
CPC .............. *A61B 5/30* (2021.01); *A61B 5/7282* (2013.01); *A61N 1/0476* (2013.01)

(58) Field of Classification Search
CPC ................................ A61B 5/30; A61N 1/0476
(Continued)

(56) References Cited

U.S. PATENT DOCUMENTS

| 2005/0090756 A1 | 4/2005 | Wolf et al. |
| 2006/0116738 A1 | 6/2006 | Wolf et al. |

(Continued)

FOREIGN PATENT DOCUMENTS

| EP | 1278064 A1 | 1/2003 | |
| WO | 2018013884 A1 | 1/2018 | |
| WO | WO-2018039648 A1 * | 3/2018 | ............... A61B 5/04 |

OTHER PUBLICATIONS

International Search Report and Written Opinion corresponding to International Patent Application No. PCT/EP2020/066125, mailed Nov. 24, 2020.

(Continued)

*Primary Examiner* — Nicole F Lavert
(74) *Attorney, Agent, or Firm* — Calyx Law LLP; Frank Gerratana

(57) ABSTRACT

A microelectrode array comprises electrodes array. Each electrode is associated with a sampling circuit for sampling an electrode signal on the electrode, a sample buffer to store a representation of the electrode signal from the electrode, and activity sensor configured to detect an electrode signal event above a predetermined threshold and to set an activity flag based on the detection. The microelectrode array further comprises control logic to activate the sampling circuit and sample buffer of an electrode to sample the electrode signal and store a representation of the sampled signal for that electrode only when the activity flag is set. Electrode signal activity is detected at the electrode level to control electrode signal sampling activity. A plurality of microelectrode arrays may be coupled in a networked configuration for scheduling and controlling transmission of stored representations of the electrode signals over a data bus to a data sink.

22 Claims, 14 Drawing Sheets

(58) Field of Classification Search
USPC .......................................................... 600/300
See application file for complete search history.

(56) References Cited

U.S. PATENT DOCUMENTS

| | | |
|---|---|---|
| 2012/0041293 A1 | 2/2012 | Levi et al. |
| 2012/0277834 A1 | 11/2012 | Mercanzini et al. |
| 2015/0173631 A1 | 6/2015 | Richards et al. |
| 2018/0246079 A1 | 8/2018 | Wang et al. |

OTHER PUBLICATIONS

Kim et al. (Apr. 2009) "Integrated Wireless Neural Interface Based on the Utah Electrode Array", Biomed Microdevices, 11(2):453-466.

* cited by examiner ized sensors, will produce data at 200 Mega-samples per second).

PROBE ARRAYS

CROSS-REFERENCE TO RELATED APPLICATIONS

This application is a United States national stage application, filed under 35 U.S.C. § 371, of International Patent Application No. PCT/EP2020/066125, filed on Jun. 10, 2020. International Patent Application No. PCT/EP2020/066125 claims the benefit of GB Patent Application No. 1908326.0, filed on Jun. 11, 2019. Each of these applications is hereby incorporated by reference in their entirety.

BACKGROUND

The invention relates to probe arrays and in particular though not exclusively, to probe arrays suitable for electrogenic cell sensing, e.g. neurophysiologic sensing for use in neural recording systems.

The brain is a network of a large number of different cells that are in constant cell-to-cell communication. Each of the 100 billion neurons in the brain is connected with approximately 10000 other neurons by means of axons, which carry action potentials (AP)—electrical signals—to communicate with other cells. Any sensorimotor information, like moving an arm or tasting something bitter, any emotion, thought or mental cognition is ultimately coded into a complex firing pattern of APs involving many cells. The more complex the task, the more cells are involved. Understanding how signals are processed in the brain in health and in disease is an area of strong scientific and medical interest. Techniques currently applied are electro-physical: in vitro models (i.e. biological preparations of cells in a Petri dish) provide better accessibility and a controlled environment, whereas in vivo models (animals) present a much higher challenge. Due to the heterogeneous cellular composition of the brain, a high number of cells need to be measured at the same time to gain any relevant understanding of the brain's activities.

SUMMARY

Existing systems utilise micromachined electrode arrays (MEAs) to provide a large number of electrodes by which electrical communication with the cells can take place. As shown schematically in FIG. 1, such MEAs 1 may be fabricated on a suitable substrate 2 such as a glass-based or silicon-based substrate, and comprise conductive paths 3 and electrodes 4 deposited on the substrate 2. Each electrode 4 comprises a region of electrically conductive metal that is electrically connected by, for example a thin metal wire or deposited track 3 to a respective connector pad 5 also disposed on the substrate 2. The connector pads 5 may be disposed around the periphery of the substrate 2 to facilitate electrical connection of each electrode 4 to external circuitry. The electrodes 4 may be brought into contact with cellular material such as brain tissue under analysis to read activity from cells by amplifying and converting to digital signals by means of analogue-to-digital converters.

The electrodes 4 can be used both for recording signals from cells and for stimulating cells by releasing small injections of current, thus providing for a bidirectional communication system with the cells. Such MEAs may be deployed for both in-vitro and in-vivo applications.

A passive MEA device has no circuitry on board, only passive electrodes and wires, and typically comprises from a few tens of electrodes to a few hundreds of electrodes. Increasing the number of electrodes is limited, because when trying to add new electrode spots on its central area, eventually there will be no space to place additional wires to connect the electrodes to external pads. This routing problem limits the number of available electrodes and consequently the number of neurons that can be sensed. Considering that the biological preparations that are placed on the device may comprise thousands of cells, this results in a spatial under-sampling, thus limiting the possibility of understanding the neuronal network features.

Some MEAs 1 may include on-board electronics fabricated on the substrate 2, e.g. in layers under the array of electrodes 4 using, for example, CMOS technology. The CMOS technology may integrate signal amplification stages onto the MEA (e.g. for improving signal to noise ratio) and/or switching structures that allow multiplexing of high density electrodes on the array by connecting and disconnecting distinct groups of the electrodes, thus limiting the number of wires necessary to electrically address all the electrodes. Examples of such CMOS monolithic biosensors may integrate 4096 electrical reading sensors in a small area arranged in a two-dimensional grid (64×64 sensor grid). Electrodes may be about 20×20 μm size and their spacing is 20 μm, thus providing a higher density compared to standard passive MEAs. Throughout this specification, the expression "biosensor" is used to refer to an array of electrical sensors/electrodes plus any other functional circuitry on a monolithic, e.g. CMOS, substrate. Individual electrical sensors on the monolithic substrate may be referred to as electrodes, channels or sensors. The area on a planar CMOS biosensor occupied by a metal electrode plus a surrounding area between it and adjacent electrodes may be referred to as a pixel.

The CMOS-MEA integrates circuitry on a board (such as signal amplification and filter stages that on passive MEAs are external) and each electrode is connected to external pads 5 through switches that allow quick reading of all the electrodes on the grid/array by connecting and disconnecting distinct groups of them, thus limiting the number of wires used to read the electrodes (e.g. all data from 4096 electrodes travel on only 16 wires). The switching is performed at high speed to allow a high time resolution for the entire array; the entire array can be sampled at, 10 kHz, 20 kHz or even higher, meaning that a single entire "frame" of activity is taken at least every 100 μs or 50 μs, for example.

The sensitivity of such CMOS-MEA systems allows recording of both fast short signals (e.g. intracellular voltage/current variations across cell membranes or extracellular spike events of about 1 ms duration occurring in dissociated cultures and tissue preparations as cerebellum or retina) and slow oscillations (typically spontaneous and evoked Local Field Potential (LFP), fEPSP or Population Spike events lasting 10 to 100 ms occurring in acute brain slices).

There remain significant problems in how to achieve even greater numbers of electrodes in terms of (i) maintaining or improving electrode density on each biosensor (i.e. the number of electrodes per unit area on each monolithic substrate) and (ii) handling data to and from ever larger numbers of electrodes. Dealing with ever larger total numbers of electrodes may arise both from a total number of electrodes on each biosensor, and/or having multiple biosensors in networked arrays, e.g. multi-chip devices operating together in an array.

Inherently, high-resolution biosensors and biosensor arrays may have at least the following characteristics: (i) they produce a large amount of data, e.g. 20 kilo-samples per second per measured electrode, which in the case of 10,000 electrodes results in data rates of 400 MB/s; and (ii) they are prone to substantial power consumption if operated continuously and in networks of chips, which may result in significant heat dissipation problems, power management problems and data management problems. Minimizing heat dissipation may be desirable especially where the electronics is in close proximity to or in contact with cells being monitored. Minimizing power consumption and data bandwidth may be beneficial especially for ultra-low power and wireless applications as for instance in-vivo applications designed for untethered animal research and for mobile human clinical use.

It is an object of the invention to provide improvements in microelectrode arrays which may assist in overcoming such problems.

According to one aspect, the invention provides a microelectrode array comprising:
- an array of electrodes,
- each electrode having associated with it a sampling circuit for sampling an electrode signal on the electrode, and a sample buffer to store a representation of the electrode signal from the electrode,
- each electrode further having associated with it an activity sensor configured to detect at least one electrode signal event above a predetermined threshold and to set at least one activity flag based on the detection;
- the microelectrode array further comprising control logic to activate the sampling circuit and sample buffer of an electrode to sample the electrode signal and store a representation of the sampled electrode signal for that electrode only when the activity flag is set.

According to another aspect, the invention provides a microelectrode array comprising:
- an array of electrodes,
- each electrode having associated with it a sampling circuit for sampling an electrode signal on the electrode, a cyclic buffer receiving the sampled electrode signals from the sampling circuit and a sample buffer to store a representation of the electrode signal from the cyclic buffer,
- each electrode further having associated with it an activity sensor configured to detect at least one electrode signal event above a predetermined threshold and to set at least one activity flag based on the detection;
- the microelectrode array further comprising control logic to gate data from the cyclic buffer of an electrode to the sample buffer to store a representation of the sampled electrode signal for that electrode only when the activity flag is set.

The sampling circuit may include, for each electrode, an ADC configured to convert the electrode signal on the electrode to a digital form and transfer the sampled electrode signal to the cyclic buffer. The activity sensor may be configured to detect the electrode signal events above a predetermined threshold based on the electrode signal in digital form from the ADC.

The or each activity sensor may be shared by a plurality of electrodes. Each electrode may have its own activity sensor separate from activity sensors for other electrodes. The or each sampling circuit may comprise an analogue-to-digital converter (ADC). The control logic may be configured to switch the respective ADC for an electrode from a quiescent state to an active state when a respective activity flag is set and to return the respective ADC from the active state to a quiescent state when any respective activity flags are not set. The control logic may be further configured to tag each sample stored in the sample buffer with an identification of the electrode from which the sample was taken and/or a time indication associated with the sample. The control logic may be configured to tag the samples in groups. The microelectrode array may be configured such that an activity flag remains set following a detected event at an electrode for a period sufficient to capture plural samples from the electrode following a detection event. The activity flag may determine a duration of sampling window during which plural samples are captured. The duration of the sampling window may be programmable. The activity flag may remain set for a period of between 2 and 200 ms or between 10 and 500 ms following detection of an electrode signal event. The control logic may be further configured to determine an activity type based on a detected event and to adapt the duration of sampling window based on the activity type. The control logic may be further configured to determine an activity type based on a detected event and to adapt a threshold level required to detect an event based on the activity type. The duration of the sampling window may have variable length based on at least one property of the electrode signal. The microelectrode array may be further configured such that, when an activity flag is set for one or more electrodes for which an electrode signal event above a predetermined threshold has been detected, activity flags are automatically set for one or more adjacent electrodes in a predetermined region of attention. The microelectrode array may be further configured to vary the number of electrodes within a region of attention according to at least one of predetermined rules and attributes of the detected electrode signal event at one or more electrodes. Each electrode may further include a range sensor configured to detect a measure of signal amplitude associated with each detected event. A range flag may be set based on the measure of the signal amplitude. The control logic may be configured to adjust a gain of the sampling circuit based on the range flag.

The or each sampling circuit may be shared by a plurality of electrodes. The or each sample buffer may be shared by a plurality of electrodes. Each activity sensor may be configured to perform the detection of a signal event based on any one or more of amplitude, spectral content and energy of the respective electrode signal event. The control logic may be further configured to generate an activity map identifying the subset of electrodes in the array for which activity is or has been detected. The generated activity map may include in the subset of electrodes one or more electrodes in a region of interest adjacent to electrodes for which activity is or has been detected. The or each sample buffer may be coupled to a data bus for transmitting stored samples to a receiver together with respective sample tags. The control logic may be further configured to sequence access to the shared sampling circuit and/or shared sample buffer by each of the plurality of electrodes for which the respective activity flag is set. Each electrode may further include stimulation circuitry for applying a stimulation signal to the electrode at times when the activity sensing is disabled. Each activity sensor may be configured to set the activity flag based on the electrode signal relationship to multiple thresholds, e.g. by the electrode signal event reaching two or more thresholds which could each relate to the same or different signal characteristics.

According to another aspect of the invention a multi-microelectrode array comprising a plurality of the microelectrode arrays described above may be arranged in a network, each microelectrode array including a status register indicating a status of at least one sample buffer of the array, and further comprising:

a network controller, coupled to each microelectrode array by a bus, the network controller being configured to schedule transmission of sample buffer contents of the plurality of microelectrode arrays over the bus according to the condition of the respective status registers.

The plurality of microelectrode arrays in the multi-microelectrode array may be arranged in a tree network comprising a root node coupled by a control channel line to each of a plurality of parent nodes. Each parent node may be coupled by a further control channel line to each of a plurality of respective child nodes. The network controller may be configured to schedule the transmission of sample buffer contents of the plurality of microelectrode arrays, over the bus, using a hierarchy of control lines. The plurality of microelectrode arrays in the multi-microelectrode array may be arranged in parallel sub-groups. Each sub-group may have a said bus and a common control channel line. The network controller may be configured to schedule the transmission of sample buffer contents of the plurality microelectrode arrays in each respective group, over the respective bus, using the respective common control channel line for that group.

According to another aspect, the invention provides a multi-microelectrode array for electrogenic cell sensing comprising a plurality of microelectrode arrays arranged in a network,
    each microelectrode array having a plurality of electrodes, each electrode having associated with it a sampling circuit for sampling an electrode signal on the electrode and a sample buffer to store a representation of the electrode signal from the electrode,
    each microelectrode array coupled to the network via a data bus and at least one control line,
    the multi-microelectrode array further including a network controller coupled to each microelectrode array, the network controller configured to schedule and control transmission of the stored representations of the electrode signals from each microelectrode array over the data bus to a data sink, using the data bus and control lines.

Each microelectrode array in the multi-microelectrode array may further comprise a status register indicating a status of at least one sample buffer of the microelectrode array. The status registers may be coupled to the network controller by the control lines. The network controller may be configured to schedule transmission of sample buffer contents of the plurality of microelectrode arrays over the bus according to the status of the respective status registers.

The plurality of microelectrode arrays in the multi-microelectrode array may be arranged in a tree network comprising a root node coupled by a control line to each of a plurality of parent nodes. Each parent node may be coupled by a further control line to each of a plurality of respective child nodes. The network controller may be configured to schedule and control the transmission of the sample buffer contents of the plurality of microelectrode arrays, over the data bus, using a hierarchy of said control lines. Each parent node may comprise a discrete microelectrode array, and each child node may comprise a discrete microelectrode array.

The plurality of microelectrode arrays may be arranged in parallel sub-groups, each sub-group having a said data bus and a common control line. The network controller may be configured to schedule and control the transmission of sample buffer contents of the plurality microelectrode arrays in each respective group, over the respective data bus, using the respective common control line for that group.

According to another aspect, the invention provides a method of obtaining electrical signals from electrogenic cell material, the method comprising:
    placing a microelectrode array comprising an array of electrodes in contact with the electrogenic cell material;
    at each electrode in the array, detecting with an activity sensor associated with the electrode occurrence of at least one electrode signal event above a predetermined threshold and setting at least one activity flag based on the detection of said electrode signal event;
    for each electrode in the array for which an activity flag is set, sampling the electrode signal using a sampling circuit associated with the electrode;
    transferring the sample to a sample buffer to store a representation of the electrode signal from the electrode,
    wherein control logic of the microelectrode array activates the respective sampling circuit and respective sample buffer for an electrode to sample the electrode signal and store the representation of the sampled electrode signal for that electrode only when the activity flag is set.

According to another aspect, the invention provides a method of obtaining electrical signals from electrogenic cell material, the method comprising:
    placing a microelectrode array comprising an array of electrodes in contact with the electrogenic cell material;
    for each of at least some of the electrodes:
    sampling an electrode signal on the electrode and storing the received sampled electrode signals in a respective cyclic buffer;
    detecting with an activity sensor associated with the electrode occurrence of an electrode signal event above a predetermined threshold and setting an activity flag based on the detection of said electrode signal event;
    for each electrode in the array for which an activity flag is set, transferring the sampled electrode signals from the cyclic buffer to a sample buffer to store a representation of the electrode signal from the electrode,
    wherein control logic of the microelectrode array transfers the data from the cyclic buffer of an electrode to the sample buffer to store the representation of the sampled electrode signal for that electrode in the sample buffer only when the activity flag is set.

The method may further comprise placing a plurality of said microelectrode arrays in contact with electrogenic cell material, the microelectrode arrays being arranged in a network, each microelectrode array including a status register indicating a status of at least one sample buffer of the array, and
    operating a network controller, coupled to each microelectrode array by a bus, to schedule transmission of sample buffer contents of the plurality of microelectrode arrays over the bus according to the condition of the respective status registers.

According to another aspect, the invention provides a method of obtaining electrical signals from electrogenic cell material, the method comprising:
    placing a plurality of microelectrode arrays in contact with electrogenic cell material;
    coupling the plurality of microelectrode arrays into a networked multi-microelectrode array, each microelectrode array coupled to the network via a data bus and at least one control line;

at selected electrodes in each microelectrode array, sampling an electrode signal on each electrode and storing, in a sample buffer, a representation of the electrode signal from the electrode, using a network controller coupled to each microelectrode array, to schedule and control transmission of the stored representations of the electrode signals from each microelectrode array over the data bus to a data sink, using the data bus and control lines.

BRIEF DESCRIPTION OF THE DRAWINGS

Embodiments of the present invention will now be described by way of example and with reference to the accompanying drawings in which.

DETAILED DESCRIPTION

Figure 1:
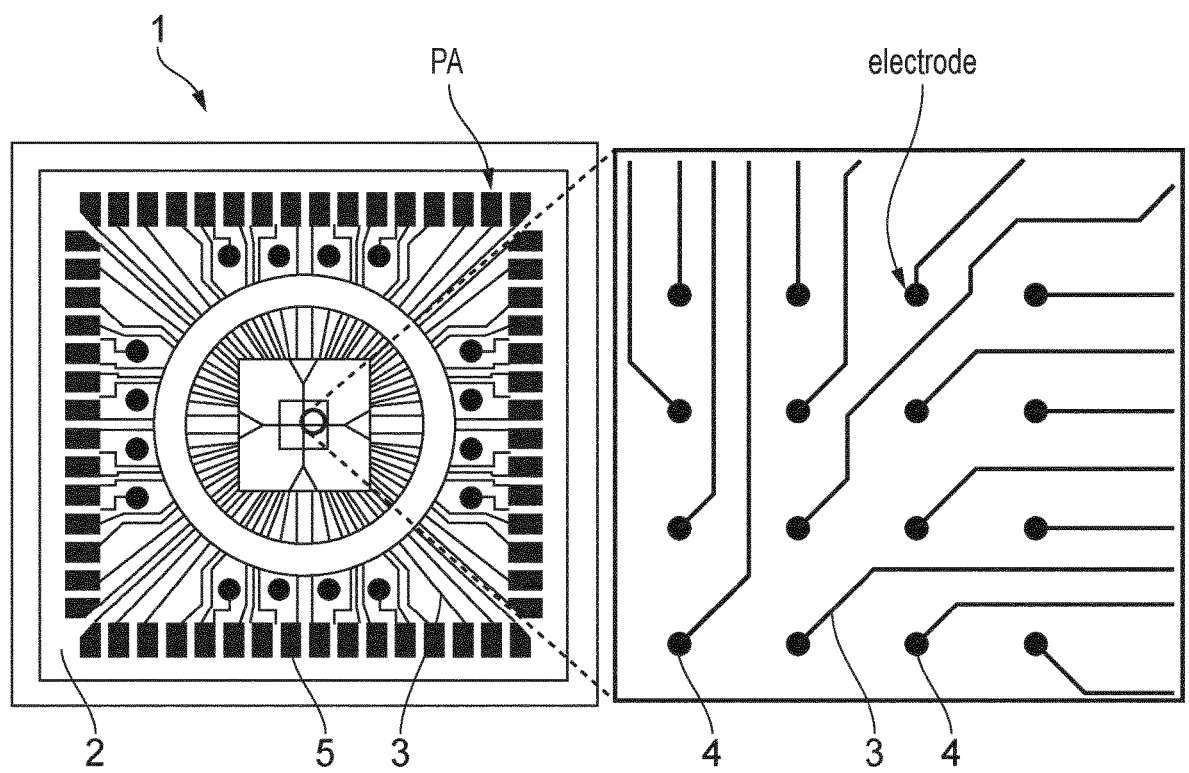
FIG. 1 shows a schematic view of an example of a prior art microelectrode array (MEA) device.

Electrophysiological data from neurons is inherently sparse. Typically, an electrode in proximity of active cells records spike or local field potential (LFP) signals between one hundredth and one thousandth of the total time on average. If not all electrodes in an array of electrodes are in contact with cells or active cells, thus resulting in 'silent' electrodes, the total percentage of time that signals from the electrodes in the array are relevant, i.e. carrying useful biological information, could be reduced to as little as 0.1-0.01%. Thus, it is highly inefficient in terms of power consumption, communication bandwidth, processing and storage demand to continuously record from all electrodes in a system. Researchers and companies working in the neuroscience domain have applied sophisticated post-processing techniques after sampling, in the digital domain, to allow detection of relevant signal events in the data set and thereby to enable data compression, to become more efficient in resource management. However, these strategies reduce consumption of resources only in the digital domain and do not solve the problem at its roots.

The present disclosure describes techniques for detecting electrode signal activity at the electrode level to thereby strategically control electrode signal sampling and/or streaming activity. This enables a reduction in power consumption and in redundant data generation by switching off components for inactive channels (e.g. ADC, amplifiers, high-speed output buffers, etc.). The total power budget and bandwidth requirements for a high-resolution MEA sensor are thereby reduced. For example, the total power budget might be reduced by 99.9 to 99.99% with substantial benefits for applications requiring networks of chips such as multi-well applications, wireless transmission, fast data processing (e.g. FPGA-based real-time closed-loop bidirectional neural interface systems), battery powering, etc At the electrode-level of each microelectrode array, a sensing and actuating device is provided. Resource allocation of a complex system requires specific decisions to be provided at a very early stage in the acquisition chain. Activity detection based on signal-specific characteristics (such as amplitude, spectral content, energy, etc.) leads to efficient distribution and allocation of the system's resources to improve the quality of the acquisition (i.e. signal-to-noise ratio (SNR)), to reduce redundant data for power optimization and to extract user-relevant parameters. Event-detection alone, generating only information on the time instants at which events occur, may not always be optimal since the type of waveform can contain important information (e.g. as required for spike sorting and classification). Therefore, the electrode signal activity detection preferably gates the sampling of a windowed portion of the signal, which contains richer and more complete information than a simple event-detection, such as spike-detectors. In some applications, it may be desirable to enable the windowed portion of the signal to include a time period prior to event detection as well as a time period after event detection. This can be useful to obtain prior information of a waveform as, for instance, in physical or biological processes involving pre-activation. Also, it may be desirable for the length of the window of signal capture to be adjustable, e.g. of different durations according to event detection criteria. This entails an activity detection that is configurable or adaptive in recording duration.

As mentioned above, electrophysiological data is sparse and it is inefficient in terms of power and bandwidth to continuously sample and transmit all data from a high-resolution MEA. In apparatus as described herein, signals from an electrode are acquired and transmitted only when there is activity on the electrode by windowing data, e.g. by sampling the electrode signal only during a specific window where the data is likely to contain relevant information. In one current design, a high-resolution MEA integrates sufficient resources to continuously acquire signals from the entire array at a sampling rate of 20 kHz and at a 12-bit ADC-resolution. It would be much more effective to utilise this capability strategically to acquire samples only at locations and times when the electrophysiological data is relevant.

Figure 5:
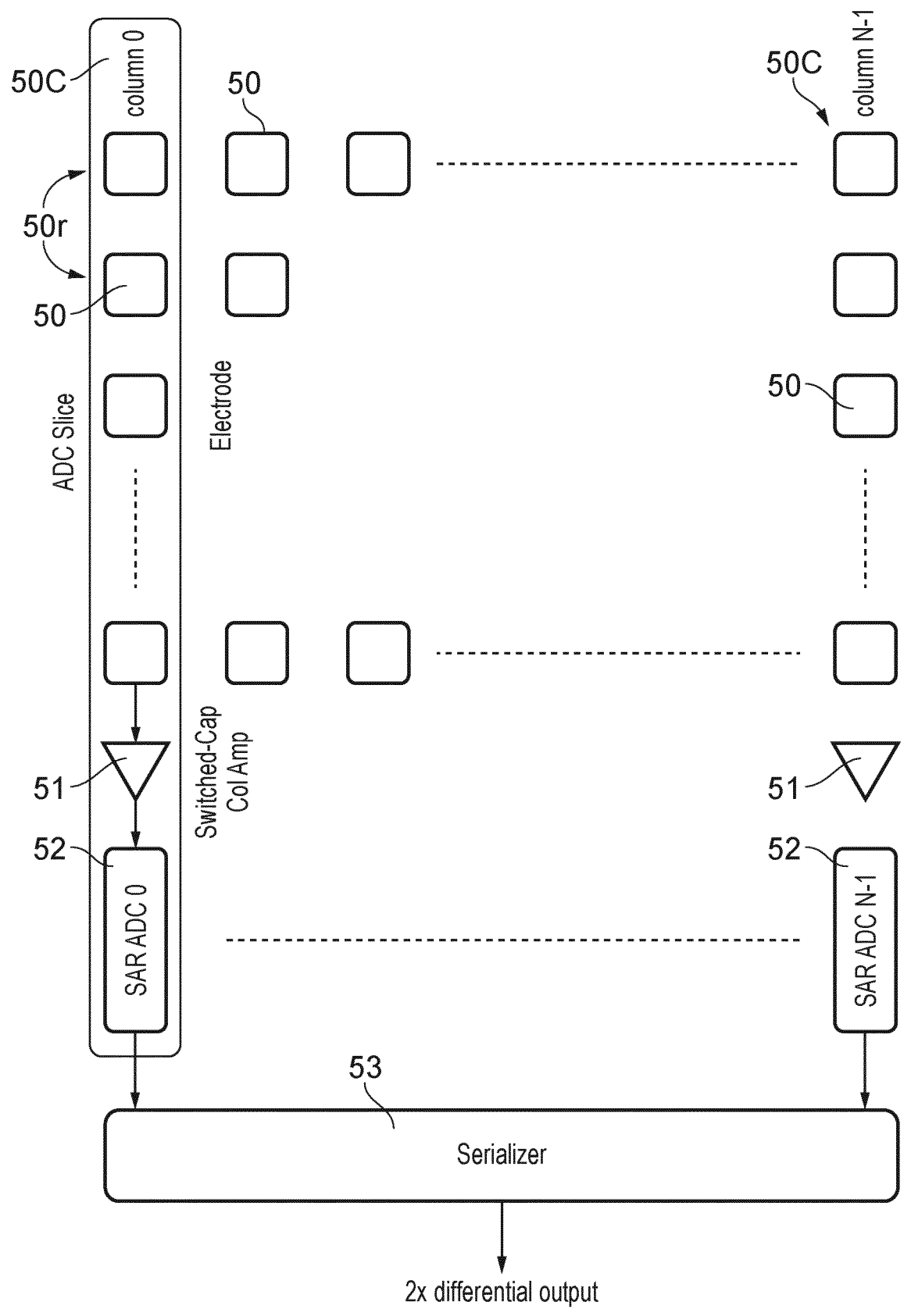
FIG. 5 shows a schematic diagram of sampling circuits for sampling and digitizing electrode signals from multiple electrodes in a microelectrode array.

With reference to FIG. 5, there is shown an active pixel-based MEA ASIC having a rectangular array of electrodes 50 arranged in columns 50c and rows 50r. Each electrode 50 may be considered as a pixel. In this example, each column 50c of electrodes 50 shares an amplifier 51 and an analogue-to-digital converter (ADC) 52. In a conventional arrangement, each electrode 50 may be sampled in turn using the shared amplifier 51 and ADC 52 providing an "ADC-slice". Many of these slices are parallelly operated to read-out the entire array at a required frame rate and the data can be transmitted using serializer 53. In some examples, an additional pre-amplifier may also be located at each pixel. Alternatively, an amplifier 51 might be located at each pixel and the ADC 52 might be shared by a group of electrodes such as column 50c.

However, since most of the time the electrodes 50 do not detect activity, in one described arrangement it is not necessary for the amplifiers 51 and ADCs 52 to sample and convert the electrode signal data during the inactive period, and the output serializer 53 would not have to stream data. Substantial circuit resources can be switched off for most of the time, or alternatively allocated to active electrodes to improve the sensing capability (e.g. to obtain better signal-to-noise ratio (SNR) per electrode by enabling more current per active electrode from a total chip current budget).

Figure 7:
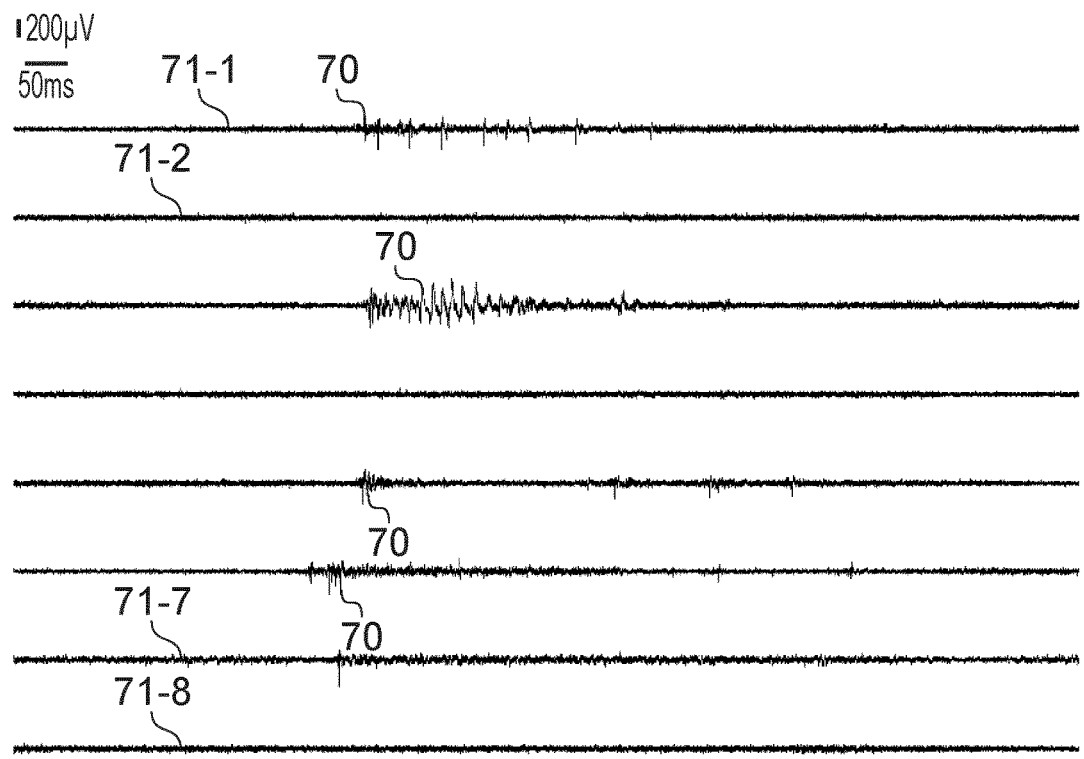
FIG. 7 shows an example of raw signals received from eight electrodes as a function of time.
Figure 8:
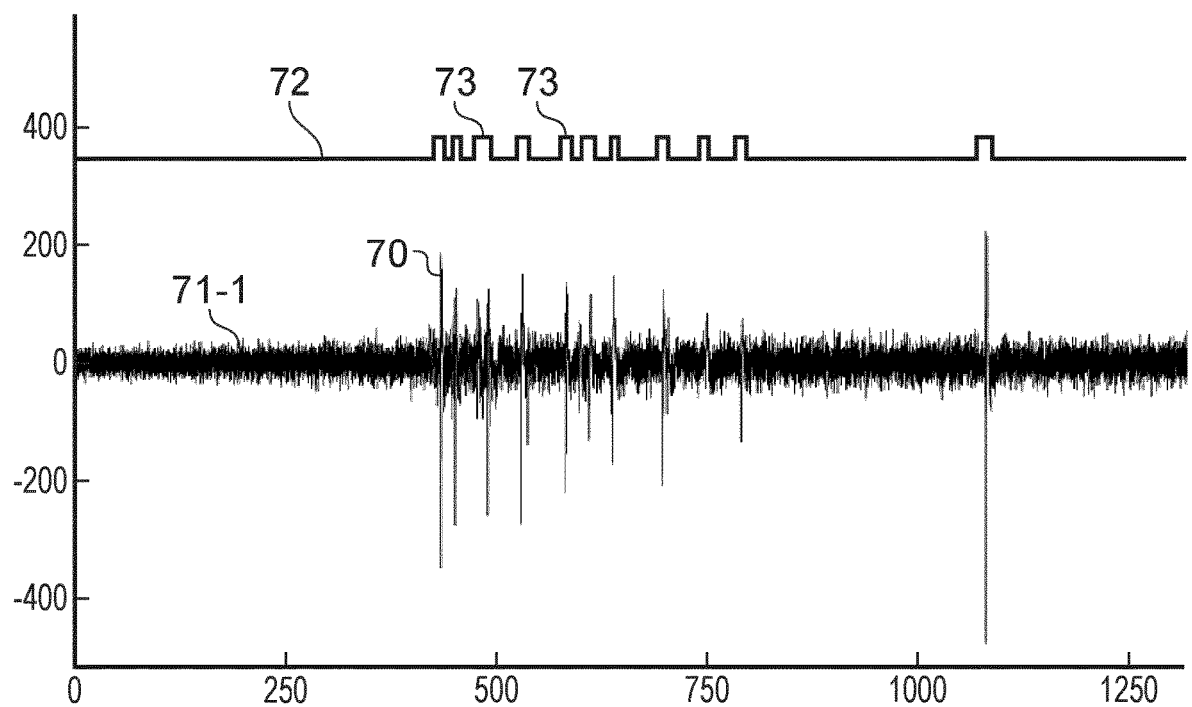
FIG. 8 shows the signal of a top electrode of FIG. 7 and an activation flag signal derived therefrom.
Figure 9:
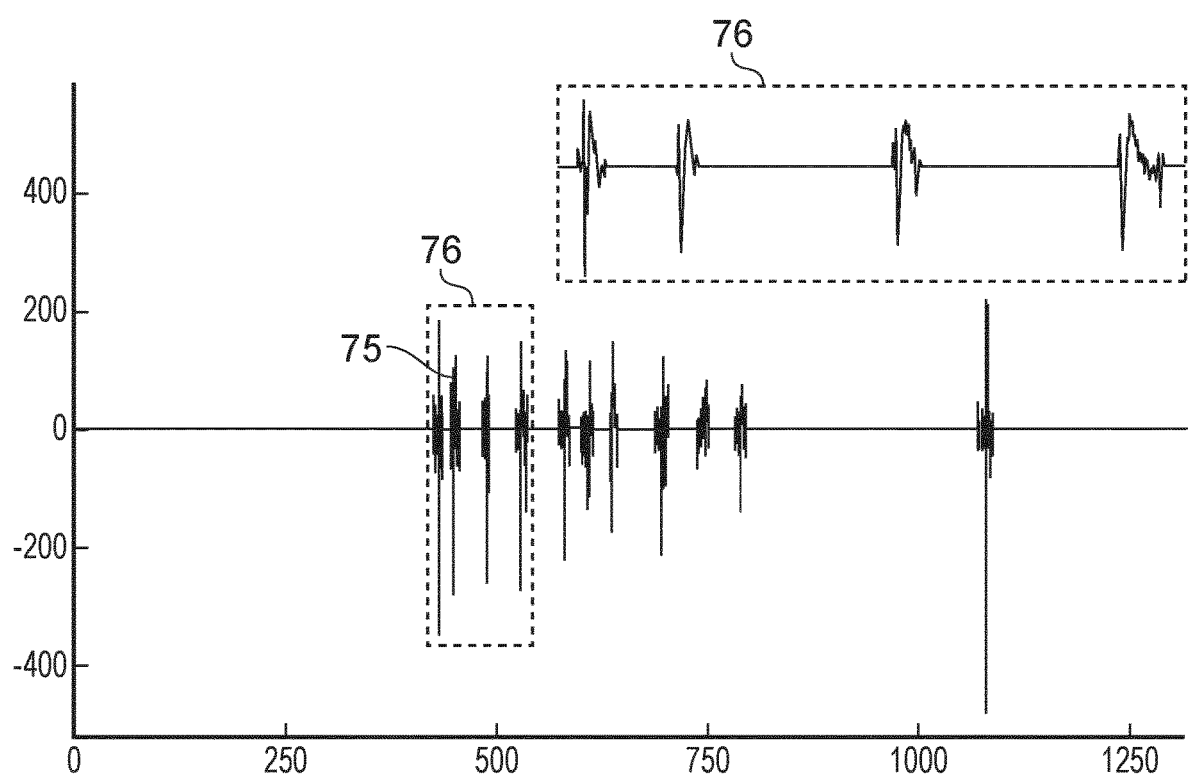
FIG. 9 shows the signal of FIG. 8 as received from the electrodes when gated by the activation flag signal and a zoom-in of a portion of that signal.

FIGS. 7, 8 and 9 illustrate the sparse nature of the electrophysiological signals 70 detected on the electrodes 50. In FIG. 7, multiple raw signals 71-1, 71-2, . . . 71-7, 71-8 (each representing e.g. voltage as a function of time) from, for example, eight continuously sampled and data-streamed electrodes 50 are shown. The relevant electrophysiological signals 70 are a small fraction of the entire streamed data since signals happen in small time windows and some electrodes can be silent, either because the coupled neurons do not respond, or because there might be no neurons coupled to those electrodes. In FIG. 8, the raw signal 71-1 of FIG. 7 is shown together with an activity signal 72 indicative of time periods 73 during which the electrode signal 70 has exceeded certain threshold criteria indicating that the electrode signal is, or may be, of interest. FIG. 9 shows the electrode signal 75 selectively sampled from signal 71-1 only during periods indicated by the activity signal 72. The signal portion 76 indicated by the dashed line is expanded in the inset.

Figure 6:
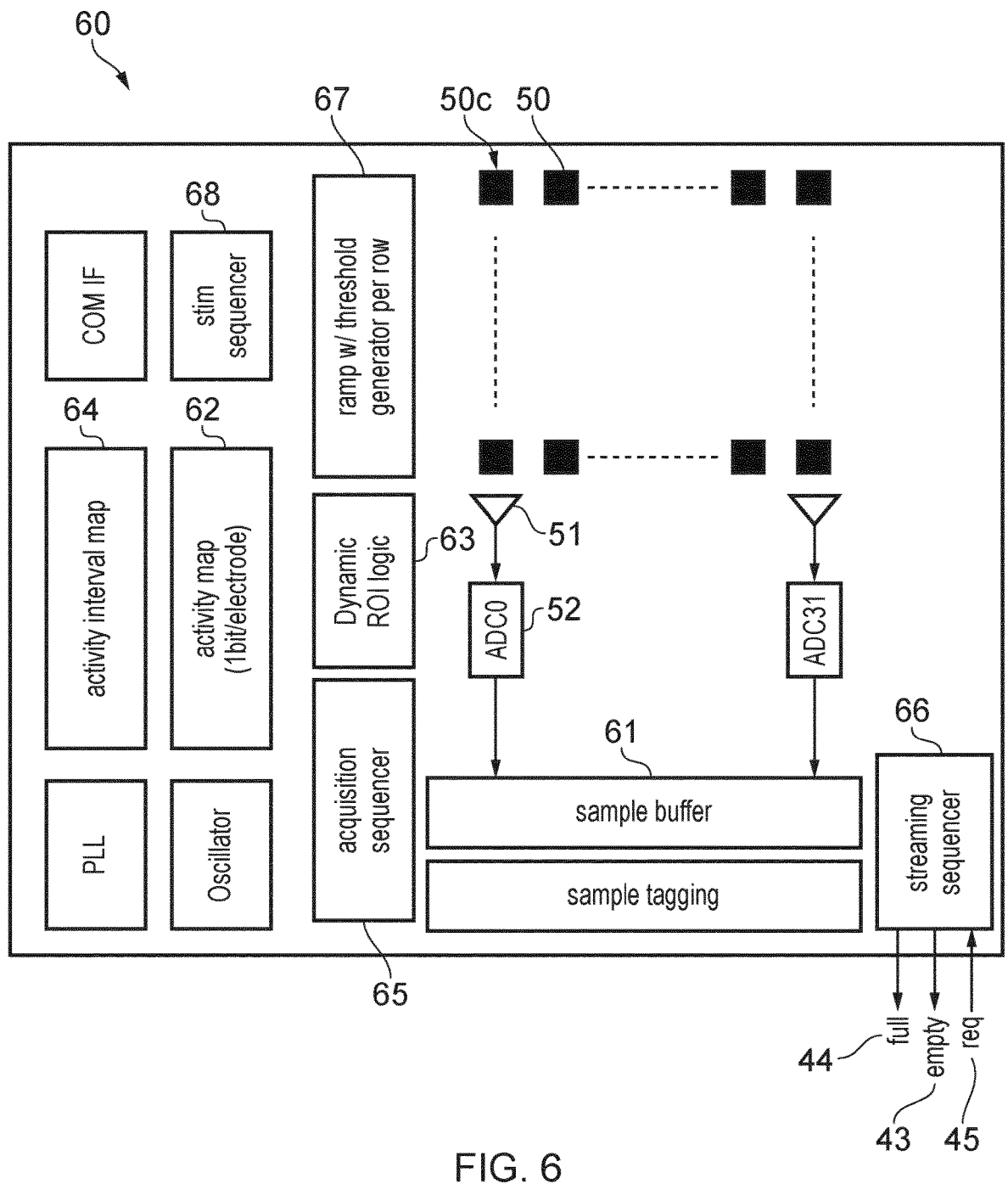
FIG. 6 shows a schematic diagram of ASIC architecture for a windowed activity sampling microelectrode array.

To achieve the selectively sampled signal 75, a high-resolution MEA ASIC is used to provide the required circuits and system infrastructure at the chip- and electrode-level. FIG. 6 shows schematically such a high-resolution MEA 60.

The MEA 60 comprises an array of electrodes 50 which may conveniently be configured in rows and columns as in FIG. 5, with electrodes 50 of each column 50c sharing an amplifier 51 and an ADC 52. However, the array of electrodes 50 could be configured in any desired pattern, including regular and non-regular spacings and distribution in other than orthogonal rows and columns. Further, although sharing the amplifier 51 and ADC 52 across an entire column is efficient in terms of silicon real estate, the amplifiers 51 and ADCs 52 may serve different groupings of electrodes 50, or may even each be dedicated to one or more electrodes. Thus, in a general aspect, each electrode 50 has associated with it a sampling circuit (e.g. 51, 52) for sampling an electrode signal on the electrode. The sampling circuits may be shared between electrodes or not shared between electrodes.

The MEA 60 also provides one or more sample buffers 61 to receive data from the ADCs 52 and to store the data therein. In a general aspect, the sample buffer 61 is configured to store a representation of the electrode signal on an electrode at a particular time, such as a digital voltage representation.

Figure 10:
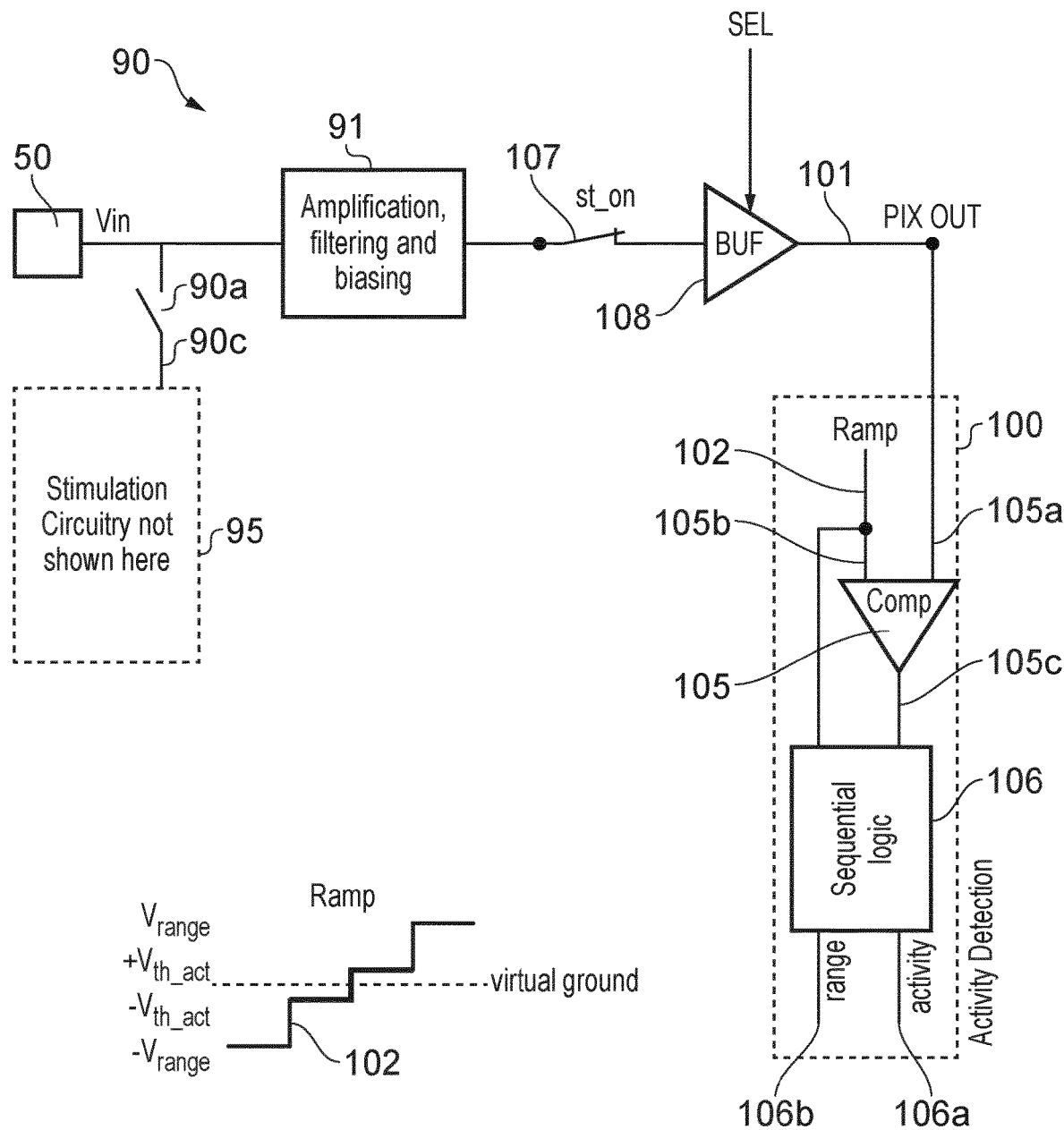
FIG. 10 shows a comparator circuit suitable for use as an electrode activity sensor and range sensor in the form of an activity discriminator and a range discriminator.

The MEA 60 also provides, for each electrode 50, at least one activity sensor (to be described hereinafter) which is configured to detect an electrode signal event above a predetermined threshold, e.g. when an electrode voltage rises above a predetermined level. The activity threshold may be fixed or adjustable, e.g. programmable. More generally, the expression 'detect a signal event above a predetermined threshold' is intended to encompass sensing or detecting any electrode signal event which achieves one or more of a predetermined condition or set of conditions indicative of a signal event of interest or a target event. The predetermined condition or set of conditions to be achieved may be fixed or adaptively adjustable, e.g. based on prior signal events detected. A set of conditions may include one or more signal conditions that are dependent on other detected conditions. The conditions indicative of a signal event greater than a predetermined threshold may include any one or more of a magnitude, a frequency and/or or intensity of any parameter associated with the signal including, e.g. a count or frequency of a succession of electrode signal events which might individually be sub-threshold, or a frequency or combination of other signal events. The expression 'above a predetermined threshold' is also intended to encompass conditions where a property of a signal achieves a certain magnitude, i.e. including where a negative-going property of the signal falls below a predetermined negative threshold. The activity sensor may comprise a discriminator such as illustrated in FIG. 10. The activity sensor may be configured to detect an electrode signal event based on any suitable parameter, such as the amplitude of the voltage or current, the spectral content or energy of the electrode signal or other property of the electrode signal waveform. The activity sensor is operative to set an activity flag indicating that the respective electrode has a signal suitable for sampling/data capture. The activity flag may be passed to an activity map register 62 which generally provides an activity map identifying all the electrodes 50 in the array for which activity is detected, or has been detected within a specified preceding time period. The activity map register 62 may be a 1-bit array of the same dimension as the electrode matrix, to store an activity flag for each electrode 50. The activity map register may therefore provide a set of flags identifying all currently active electrodes within a dedicated framebuffer memory. These flags can be used to gate sampling only when activity is detected.

The MEA 60 may also provide, for each electrode 50, at least one range sensor (to be described hereinafter) which is configured to detect a signal amplitude associated with each detected electrode signal event. The range sensor may comprise a discriminator such as illustrated in FIG. 10. The range sensor is operative to set a range flag based on, for example, the detected signal amplitude. More generally, the range sensor may set the range flag based on detected power, energy or any other measure of or related to signal amplitude in the time or frequency domain. Multiple range flags could be used based on different properties. This range flag (or flags) may be used to set or control a gain of the amplifier 51 and/or of the ADC 52 of the sampling circuit such that any sampling of the electrode signal can be performed under optimal sampling conditions. Thus, in one example, the range flag enables scaling the input range of the ADC to maximize the achieved resolution depending on the voltage level of each electrode.

The activity flag (and range flag, if applicable) for each electrode 50 may be passed to control logic, such as a dynamic region-of interest logic module 63 or acquisition sequencer 65. The expression "activity flag" as used herein is intended to encompass any suitable electronic indication/control signal capable of indicating that an electrode signal event of interest or target event condition has been detected by an activity sensor and which can be used to control operation of sampling and/or storing and/or gating of an electrode signal from an electrode or group of electrodes.

Based on the activity flag or flags, the dynamic ROI logic module 63 allocates the required ADC-slices for electrode sampling accordingly. An activity interval map 64 is a programmable register bank that contains an activity window counter for each electrode 50. Once an electrode is activated (by setting the respective activity flag), the activity window counter counts down a predetermined time and the activity window expires when the counter reaches 0, at which time the activity flag for that electrode can be unset, e.g. returned to 'off' state or 'zero'. In this respect, the activity flag may remain set following a detected event at a respective electrode for a predetermined period. The predetermined period may be established as a period sufficient to capture and store sufficient consecutive samples to capture important features of any signal event of interest. In an example, a duration of the predetermined period determining the sampling window duration may lie between 2 and 200 ms in the case of spiking or bursting activity/events, or between 10 and 500 ms in the case of LFP or ictal activity/events. The activity sensor may be configured to determine an event type in order to establish the appropriate predetermined period, the system could be pre-programmed with a window duration appropriate to the signal analysis application. In one arrangement, the activity sampling window can be made adaptive (e.g. in duration) by introducing a termination event requirement in the control logic that can be based on any suitable parameter from the detected signal, reflected in very specific states of the activity flag or flags or the type(s) of activity flag(s). Thus, in a general aspect, the sampling window may have a duration which is adaptive based on at least one property of an electrode signal, e.g. requiring the detection of a further signal property relative to an appropriate threshold (e.g. a 'termination event') in order to determine that an activity flag should be unset (e.g. reset or 'cancelled'). The further signal property required to unset the activity flag could be, for example, falling below the predetermined threshold that triggered this initial setting of the activity flag (or a different threshold), or detection of some other condition(s) indicative that the signal is no longer of interest (even where it may still remain above the predetermined threshold). The unsetting/resetting of the activity flag could be immediate on detection of the termination event, or it could follow a time-out period following the detection of the termination event.

The dynamic ROI logic module 63 may dynamically manage the resource of an ADC-slice 50c between all the active electrodes belonging to the slice. If all electrodes of a slice were to be active, it would effectively provide serial addressing logic. However, where there is changing activity on subsets of electrodes, then the dynamic ROI logic module 63 may decide how ADCs 52 can be switched on and off to save power or how to change electronic parameters to improve front-end performance such as biasing, or channel bandwidth to adapt the system noise bandwidth always to the minimum needed for a multiplexed channel in order to reduce aliasing. Aliasing can be an inherent drawback of highly multiplexed systems. In another aspect, the dynamic ROI logic module 63 could also include a predictor/estimator with self-learning abilities.

An acquisition sequencer 65 generates control and address signals to sample all the active electrodes 50 (i.e. those with the activity flag set, such as in an 'on' state or 'one' state) using the sampling circuits comprising amplifiers 51 and ADCs 52. The acquisition sequencer manages the column amplifier 51 gain settings based on the range flag from each electrode 50, generates the required timings to use the available resources (e.g. ADCs, amplifiers, etc.) managed by the dynamic ROI logic 63 and synchronizes the generation of the voltage levels distributed to all or groups of electrodes as references (e.g. a voltage ramp). All samples flow into the sample buffer 61. A sample buffer 61 is preferred because the data stream is not continuous due to the dynamic allocations of active regions of interest, or because the data bus to transmit data samples to a downstream receiver (e.g. off-chip) may be shared with other MEAs 60 and may be busy. The acquisition sequencer 65 exemplifies control logic to activate the sampling circuit 51, 52 and sample buffer 61 to sample the electrode signal of an electrode, and to effect storage of a representation of the sampled electrode signal for an electrode only when an activity flag is set.

In the example of FIG. 6, the sample buffer 61 may be organized into columns. Before streaming the data, each sample is preferably tagged, e.g. with a dynamic tagging mechanism, with the identity of the electrode 50 from which the sample was taken, for later identification. Tagging each sample may comprise tagging each sample individually, or tagging groups of samples such that the samples within the group effectively share a common tag. The tagging preferably also includes the timing of the sample or group of samples. The tagging may include the timing of the sampling window to which the sample or samples relate. In general, a time tag may provide an indication of a time associated with the sample, e.g. real sample time, relative sample time or window time and/or length. The tagging is because the read-out scheme is not a fixed serialised data stream having samples taken serially from each electrode in turn, due to the dynamic ROI logic module 63 control of sampling. In a general aspect, the acquisition sequencer 65 may also exemplify control logic configured to tag each sample stored in the sample buffer with an identification of the electrode from which the sample was taken.

A streaming sequencer 66 may be used to control an external bus for transmitting the stored data to an off-chip receiver, e.g. by communication over empty, full and request signal lines 43, 44, 45. The streaming sequencer may have to comply with continuously changing bandwidth requirements due to the sparse nature of data.

A ramp generator 67 may be provided, which may be shared across all activity sensors, to generate a voltage ramp for the activity threshold and the range voltage threshold, to be described hereinafter. The ramp generator 67 is preferably programmable, e.g. to enable adjustment of activity thresholds. Alternatively, several ramp generators 67 may be provided, each one associated with one or more activity sensors. Other arrangements can be used to generate suitable reference voltages for one or more activity thresholds.

An example of an implementation of an activity sensor (e.g. activity discriminator), and range sensor (e.g. range discriminator), circuit 100 is shown in FIG. 10. An amplification, filtering and biasing circuit 91 is coupled to a respective electrode 50 to receive an electrode signal therefrom and to amplify and, if necessary, to filter and/or bias the electrical signal according to known techniques. The amplified/filtered electrode signal at output 101 from electrode 50 is coupled to a first input 105a of comparator 105 of the activity discriminator and range discriminator 100. A ramp signal 102 is coupled to a second input 105b of comparator 105. The comparator output 105c is coupled to sequential logic 106, to provide an activity output 106a and a range output 106b. The activity output 106a is used to set the activity flag and the range output 106b is used to set the range flag as described above. The active electrode structure is bidirectional, i.e. it is also programmable so that each electrode can act as a stimulation electrode as well as a sensing electrode. Stimulation circuitry 95 may be coupled to the electrode 50 via a switch 90a operable to connect a stimulation line 90c to the electrode for use when an electrode 50 should be used to deliver a stimulation signal. A switch 107 in front of the pixel output buffer 108 driven by the same signal used to drive switch 90a for stimulation may be used to disconnect the output and tie the buffer input to GND, which ensures that the activity threshold is not overcome when the electrode is in stimulation mode.

A centralized and programmable DAC may be provided on-chip, which allows the activity sensing threshold value to be set. The DAC is cyclically programmed with the range and threshold levels to allow the activity and range circuitry within each pixel to make a decision. The programming of these DACs may be static (at the beginning of a sensing period) or may be dynamic (adaptive) operation.

The purpose of the activity discriminator and range discriminator circuit 100 may be two-fold: (i) electrode activity can be detected based on multiple threshold levels (+/−Vth_act in FIG. 10) and (ii) the signal range can be determined (with Vrange 106b in FIG. 10) and used in subsequent column-amplifier stage to adapt/change the gain. Such a variable gain allows to achieve a superior resolution of the SAR-based ADC slice, depending on the input signal amplitude (biological signals can have a wide dynamic range). Moreover, an in-pixel comparator can be designed with relaxed performances (e.g. offset voltage and input noise) as opposed to any whole in-pixel ADC solutions that would entail strict comparator requirements.

The activity discriminator circuit 100 provides for in-pixel detection of sparse signals and selective operation, for the controlling ("gating") of the required ADCs 52. It allows sampling only when there is activity detected and helps to reduce redundant data generation and power consumption. Windowing of sampling based on sensed activity or activity patterns detected inside the pixel can beneficially influence later stages of the signal processing chain to improve sensor performance in terms of noise, power consumption and data reduction. In-pixel multi-level threshold detection to control variable (column) gain amplifiers enables increasing the achievable ADC resolution by scaling/amplifying lower level input signals accordingly to the full ADC-range.

Where a sampling circuit is not required for any of the electrodes it serves, all or part of it may be powered down from an active state to a quiescent state to reduce power consumption on the MEA. The expression 'quiescent state' is intended to encompass any state using reduced power from the active state, e.g. inactive, reduced power or powered down states. Alternatively, an ADC 52 for a quiescent electrode could be deployed with increased sampling rate for other ones of the electrodes that are currently active Although the activity sensors have been described as operative to set a respective activity flag in the activity map register 62 corresponding to the electrode 50 for which activity has been detected, the activity map flags could also be set for adjacent electrodes to the electrode at which activity has been sensed such that sensed activity in one or more electrodes causes surrounding electrodes or a particular region of electrodes to become actively sampled even though those electrodes did not detect activity themselves. Such a region of electrodes that becomes actively sampled based on sensed activity of one or more electrodes within the region may be referred to as a 'region of attention' or 'region of interest'. This may be useful for ensuring capture of additional data where activity is moving. This may also be useful for sorting and spatial localisation of a signal source when the same signal source can be sensed by multiple nearby electrodes but only on a certain electrode is the signal sufficient to trigger the activity sensor. This latter strategy of triggering sampling for a 'region of attention' may have the additional benefit of enabling a higher threshold to be used, thereby reducing noise/false positives, since there is an increased likelihood of at least one electrode of several sensing a signal of interest in the region. Thus, in a general aspect, the system may be programmed to vary the number and relative positions of electrodes within a region of attention for which activity tags will be set according to predetermined rules or logic and/or attributes of the detected signal event at one or more electrodes.

For example, in a square array, when activity has set an activity flag for, and therefore started a sampling window on, a certain electrode, the same window (i.e. temporally aligned) for the four nearest adjacent electrodes or even for the eight nearest electrodes (according to preference) may be set. Among the scope or region of interest (nearest electrodes), the union of all the windows determined by the electrodes may be computed and saved for all the electrodes within the scope. To sample adjacent electrodes, unused ADC resources could be redirected. The orchestration of these tasks may be performed by the dynamic ROI logic 63.

The assertion of an activity flag can be dynamically configured, e.g. in the duration for which it remains set and the signal threshold level at which it will be triggered. This enables adaptation of the system to the nature of the activity to be detected and signals captured. This includes threshold detection according to voltage amplitude, spectral content or energy for example, for detection and triggering by spikes, bursts, LFPs etc.

The nature of the activity, e.g. the type of signal such as bursts, single spikes or field potentials may be optionally determined by an on-chip logic discriminator that feeds back the result to update the configuration parameters for each electrode. These configuration parameters may include one or more of window duration (e.g. as set in the activity interval map 64), threshold level required to detect an event (e.g. as established by ramp generator 67), number or range of adjacent electrodes for which activity flags should be set following a detection event in an electrode, disablement of electrodes, etc. The configuration parameters to be updated may be in respect of future events for the same electrode. The configuration parameters to be updated may be in respect of other electrodes in the array than the electrode or electrodes for which the nature of an activity has been detected.

In general, the control logic and control logic modules described herein may be implemented in any suitable hardware implementing the logic functions such as dynamic ROI logic 63 and acquisition sequencer 65, e.g. using general purpose digital circuitry suitably programmed or with customised digital and/or analogue circuitry implementing such logic, or a combination of both.

A further aspect of handling data from increasing numbers of electrodes is discussed in the context of providing networked arrays of MEA biosensors or multi-chip biosensors. There is a need to scale up the number of MEA chips in networked arrays, particularly for in vitro applications, from single well devices to multi-well plate devices providing, for example, 6, 24, 48 or more wells, each well containing an MEA-chip sensor, which in turn can integrate thousands of electrodes, e.g. 96 wells each with 1000 electrodes per well giving 96000 electrodes on the same device. There is a further need to scale up the number of MEA chips in networked arrays for in vivo applications, for example where multiple chips can be placed in different brain areas according to the sensorial or motorial areas to be addressed for BCI (brain-computer interface) applications.

Multi-MEA applications with high-density sensing and actuating capabilities physically build networks of nodes, each one consisting of a single MEA-ASIC. Massively parallelized recording and stimulation in in-vitro (drug screening) and in-vivo applications (brain-machine interfaces) face new challenges. With increasing number of sensors/actuators to be integrated into the wells, or in different brain areas, interconnection, interfacing and communication for smart high-throughput electrophysiology devices become relevant and require innovation and optimization at different levels to handle the immense amount of extracted data. The network's node provides local circuit infrastructure to allow self-organizing networks ("smart networks").

Figure 2:
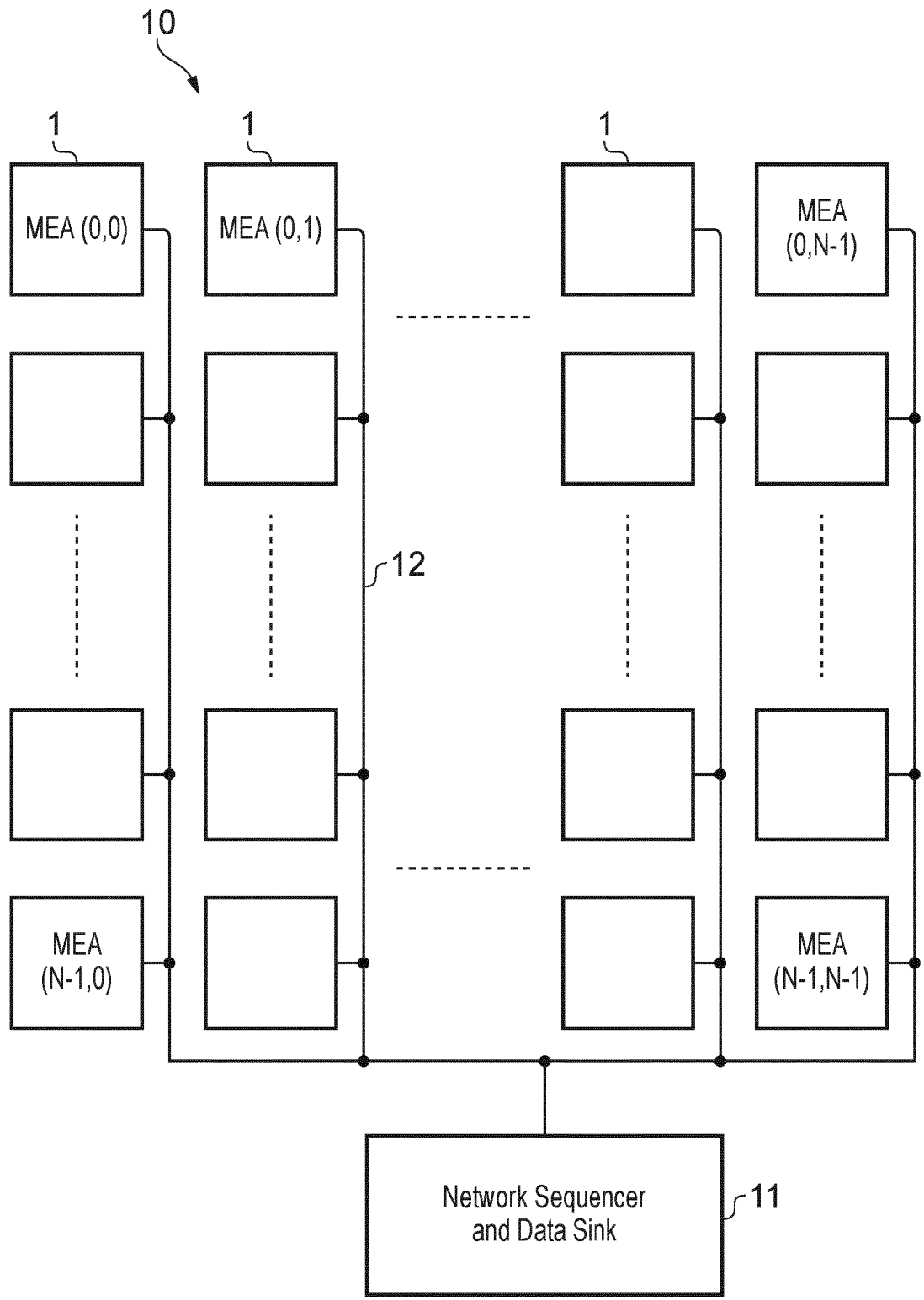
FIG. 2 shows a schematic diagram of a network of microelectrode arrays sharing a common data and control bus.

FIG. 2 illustrates a network 10 of MEAs 1 each coupled to a network sequencer and data sink 11 by way of a common data bus 12. Each MEA 1 may comprise the features of the MEA 60 of FIG. 6 so that sampling of electrodes occurs only when signal events are detected. This substantially reduces the demand on the data bus 12 and network sequencer 11 when sample data is being transferred from the on-chip sample buffers 61 in each MEA.

Figure 3:
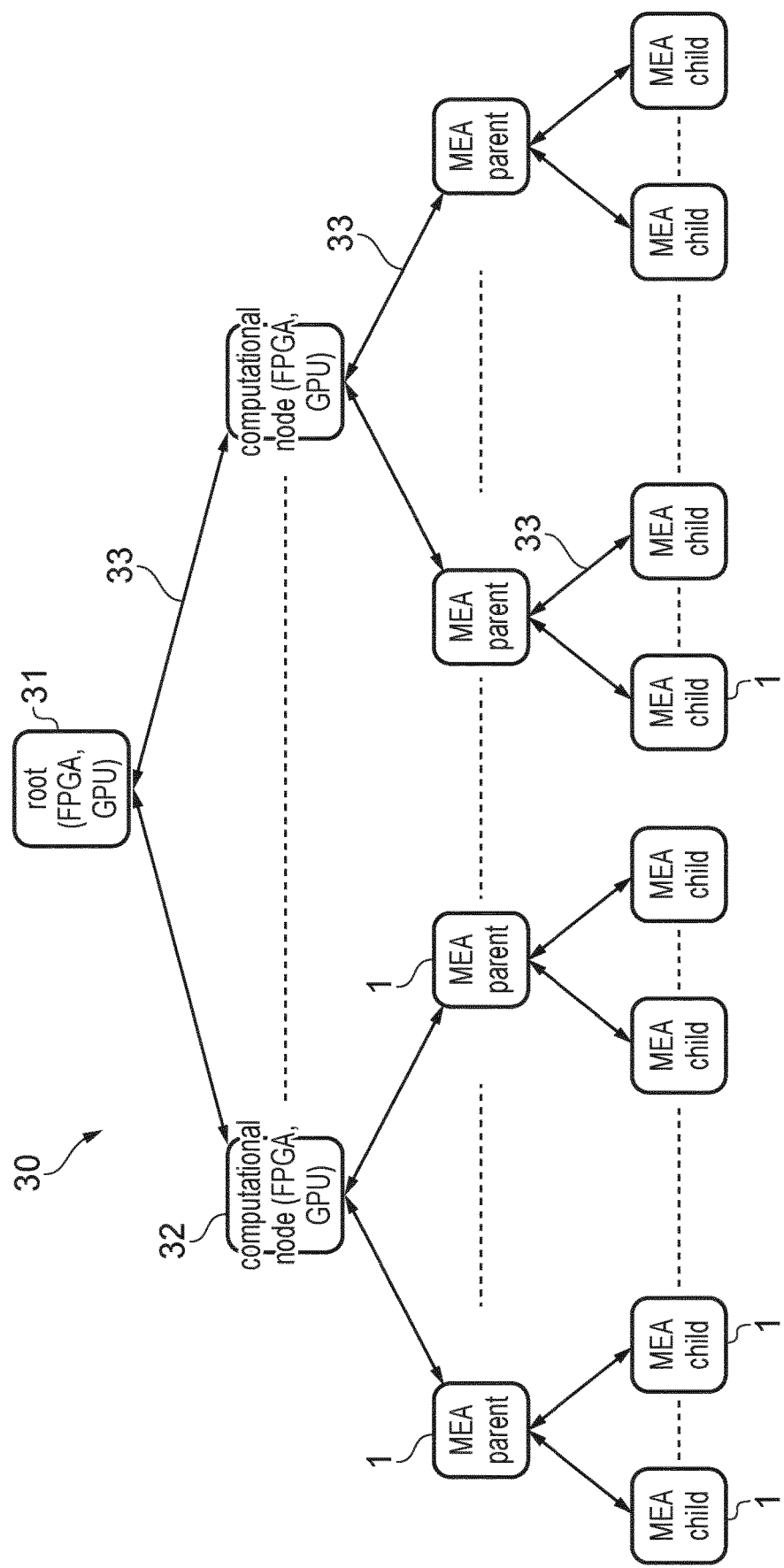
FIG. 3 shows a schematic diagram of a hierarchical network of microelectrode arrays in a tree configuration.

FIG. 3 illustrates a network 30 of MEAs 1 in a tree hierarchy. Each MEA 1 may comprise features of the MEA 60 of FIG. 6 so that sampling of electrodes occurs only when signal events are detected. Each MEA 1 within the network 30 is a child or a parent within an interconnected wired network of ASICs. The root 31 and/or sub-roots 32 of such a network consist of computational units/nodes, preferentially FPGAs (field programmable gate array), CPUs (graphical processing units), application specific processors (i.e. vector-based processors) or dedicated "brain signal processor units" (BSPU) with functions as described hereinafter. The interconnection 33 between the nodes 1 is preferably bidirectional high speed bus, for both recording and stimulation purposes. The purpose of each node in the network is two-fold: (i) collecting or sending massive data sets from or to multiple areas/MEAs and (ii) providing local circuit resources and system infrastructure to process the data to reduce power and data redundancy (and therefore, to reduce system bandwidth requirements). The root 31 and/or sub-roots 32 could themselves also comprise MEAs in addition to the computational and control functionality.

All MEAs 1 or subgroups of MEAs may access a common shared high-speed bus 33 for data transmission between the nodes, or from child node to parent node, and from parent node to the root or sub-root node, which are specific computational nodes for signal and network analysis.

Each node 1 (parent, child, etc.) has some status flags and control signals to indicate the state of its internal sample buffers 61 and to receive requests from the parent node 1 or (sub-root node 32) to dynamically transmit data within the network. The control, status and data interfaces may be shared within groups and sub-groups of the network to keep the pinout of each node (i.e. ASIC) as low as possible. The (sub-)root node(s) 31, 32 orchestrate the read-out of sample buffer data from each child node 1 and grant access to the data bus following a suitable procedure/read-out algorithm. A sequencer in the root node 31 controls the data paths of the high-speed bus system and the status flags.

Figure 4:
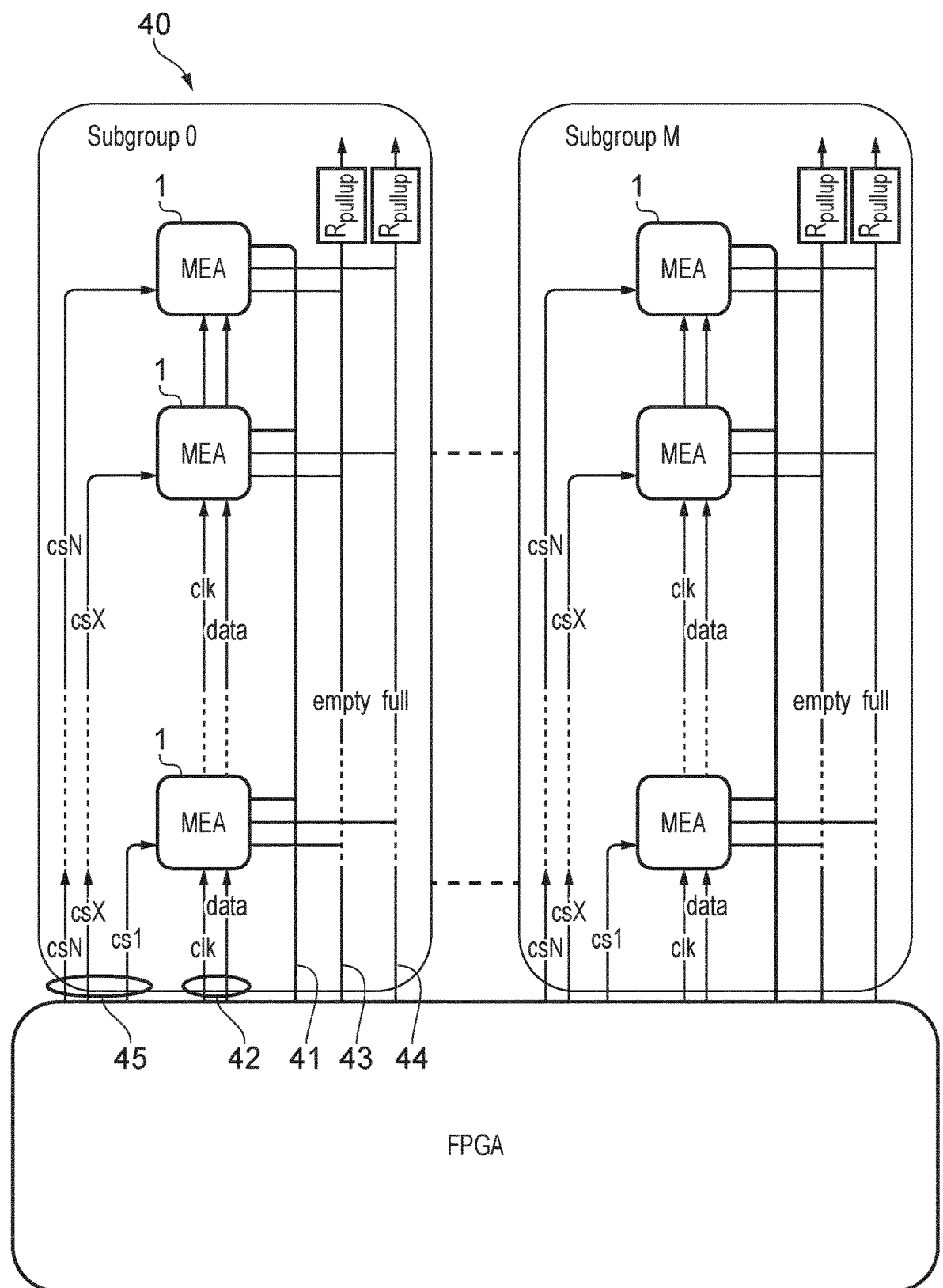
FIG. 4 shows a schematic diagram of a flat network of microelectrode arrays in a parallel architecture.

A particular implementation 40 of the general networked architecture shown in FIG. 2 and/or 3 is depicted in FIG. 4. The purpose of this particular architecture is the lowest possible pad number per ASIC to enable MEA-networks with high numbers of ASICs for multi-well applications (e.g. 96, 384 wells). Each node 1 may have the following properties:

All MEAs or subgroups of MEAs access a common shared high-speed bus 41 for data transmission between the nodes 1, or from child node to parent node, and from parent node to the root 31 (FIG. 3) or sub-root 32 (grandparents, great-grandparents, etc.)

A control upstream channel 42 (to the MEAs 1) interconnects all nodes 1 together for programming each node 1 in the network individually. This control channel 42 consists of a low number of physical lines (e.g. one or more control lines) to reduce interconnection and wiring. One suitable approach is to connect all control registers of all nodes in a serial register chain. The root 48 or sub-roots of the networks (i.e. computational unit) may be the master of the control channel 42.

Each node 1 (parent, child, etc.) has some status flags to indicate the state of its internal sample buffers. Each node accesses a shared empty-signal line 43 and full-signal line 44 that can be pulled low by the respective node 1 when the node is interrogated by its respective 'chip select' signal line 45.

Each node receives a 'chip select' signal from its responsible root 48. These individual addressing signals allow to request the status flags of a specific chip and grant access to the shared data bus.

The root node 48 orchestrates the read-out of each node 1 and grants access following a suitable procedure/read-out algorithm. A sequencer in the root node 48 controls the data paths of the high-speed bus 41 system and the status flags.

Thus, in a general aspect, and with further reference to FIG. 6, each microelectrode array (e.g. 60) includes at least one status register (not shown) which indicates a status of the one or more sample buffers 61 in the MEA 60, e.g. on status lines 43, 44. The network controller (e.g. 48 in FIG. 4) is configured to schedule transmission of the sample buffer 61 contents of the plurality of microelectrode arrays 1 over the bus 41 according to the condition of the respective status registers.

The activity map (e.g. from activity map register 64) for each MEA can be transmitted interleaved to the sampled data on the data bus (e.g. bus 41) and made available to the responsible computational node (e.g. at network controller 48) for real-time activity pattern estimation (i.e. artificial neuronal networks, machine learning, etc). The activity map may be used, for example, to define and/or adapt a read-out strategy from the ADCs 52 to the sample buffer or buffers 61, and/or a read-out strategy from the sample buffer or buffers 61 to a suitable off-chip data sink, e.g. by the network controller 48 over the bus 41, dependent on available bus bandwidth. The activity map may also serve as, or serve as basis for creating, a high-level representation of cell or brain activity. This may be useful as a compressed representation or summary of activity which could be used for characterization or prediction by machine learning or artificial intelligence (AI) algorithms. The activity may can also be used to dynamically allocate ADC resources to optimally sample the "tissue under test" with the available infrastructure.

The sample buffers 61 temporarily hold a number of samples of all currently active electrodes while the high-speed data bus is busy. The number of samples each buffer can hold may be fixed or programmable.

A programmable rule-based state machine may be provided to manage ROIs, regions of attention or prediction of next active electrodes and to allocate the available chip resources (e.g. ADC slices, buffer memory). A programmable state-machine (e.g. stimulation sequencer 68 as seen in FIG. 6) may be provided for the generation of complex high-resolution stimulation patterns to be delivered to selected electrodes, e.g. via the respective switches 90a and stimulation lines 90c exemplified in FIG. 10.

Various alternative arrangements to those discussed above are envisaged. For example, with reference to FIGS. 12 and 13, various modifications can be made to the activity sensing strategies.

Figure 12:
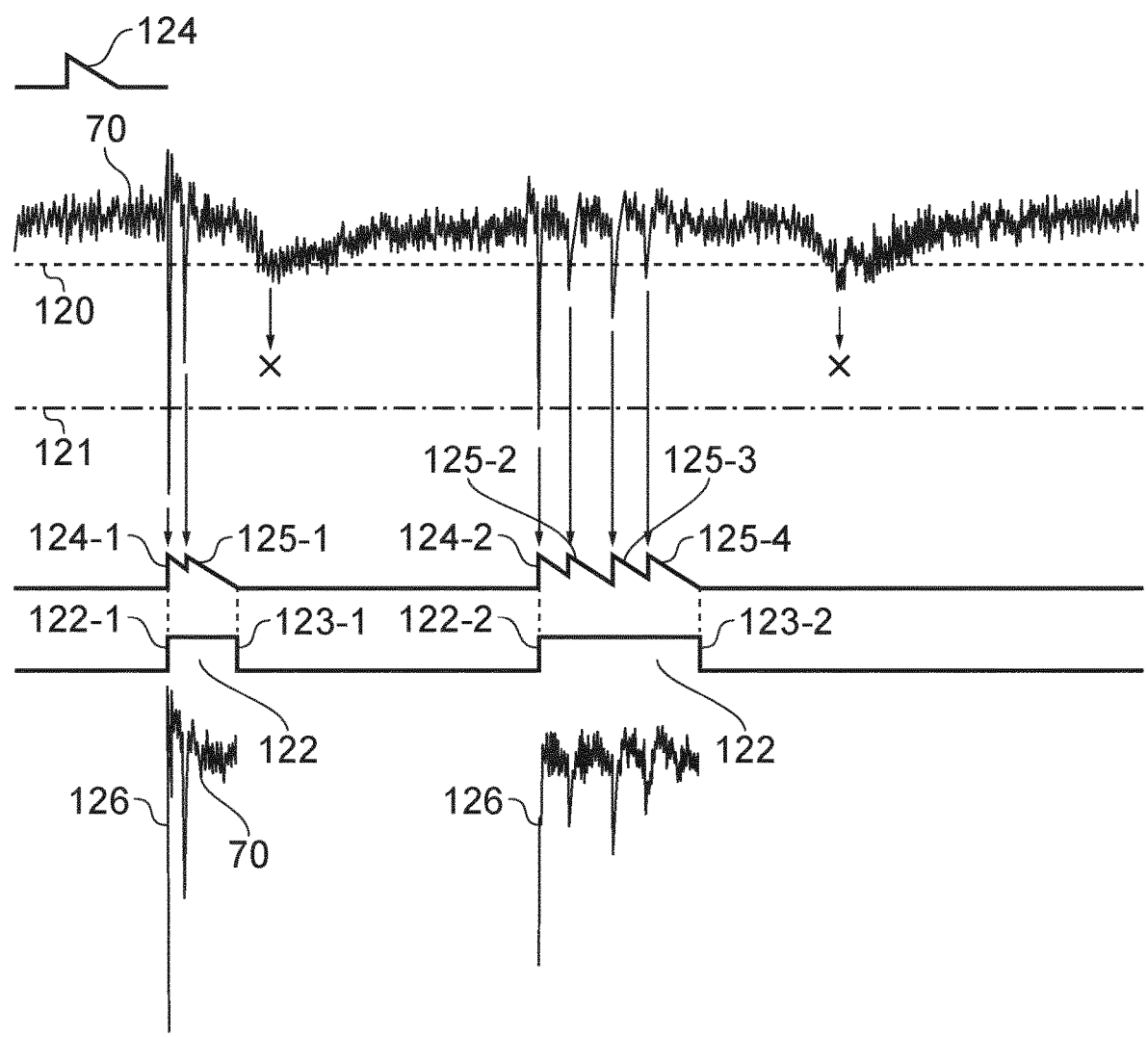
FIG. 12 shows an example of an electrode signal together with variable length sampling window signals and sampling window counter signals as triggered by lower and upper thresholds applied to the electrode signal.

FIG. 12 illustrates an activity sensing strategy in which the duration of the sampling window 122 (also exemplified by time period 73 of FIG. 8) can be automatically varied according to properties of the electrode signal 70. Two different thresholds, a lower threshold 120 and an upper threshold 121 may be generated by a DAC associated with an electrode, e.g. a DAC that is specific to the individual electrode or shared by a plurality of electrodes. The upper threshold 121 may be used to trigger the start 122-1, 122-2 of an activity (sampling) window 122. At substantially the same time, a programmable counter 124 starts counting down as seen at 124-1 and 124-2, e.g. triggered by the signal reaching the upper threshold 121. The count down may count each sample. The end 123-1, 123-2 of the activity window 122 may be defined/triggered by the counter reaching zero. However, in this arrangement illustrated by FIG. 12, the counter 124 may be reset if the signal subsequently reaches the lower threshold 120 while the counter is still active, e.g. as shown at 125-1, 125-2, 125-3, 125-4. In this way the duration of the activity (sampling) window 122 is defined by the signal remaining below the lower threshold level 120 for a programmable minimum time 124 and the window 122 of the selectively sampled signal 126 can have a variable and adaptable length based on at least one property of the electrode signal, e.g. how long it stays above a lower threshold after being triggered by an upper threshold.

Figure 13:
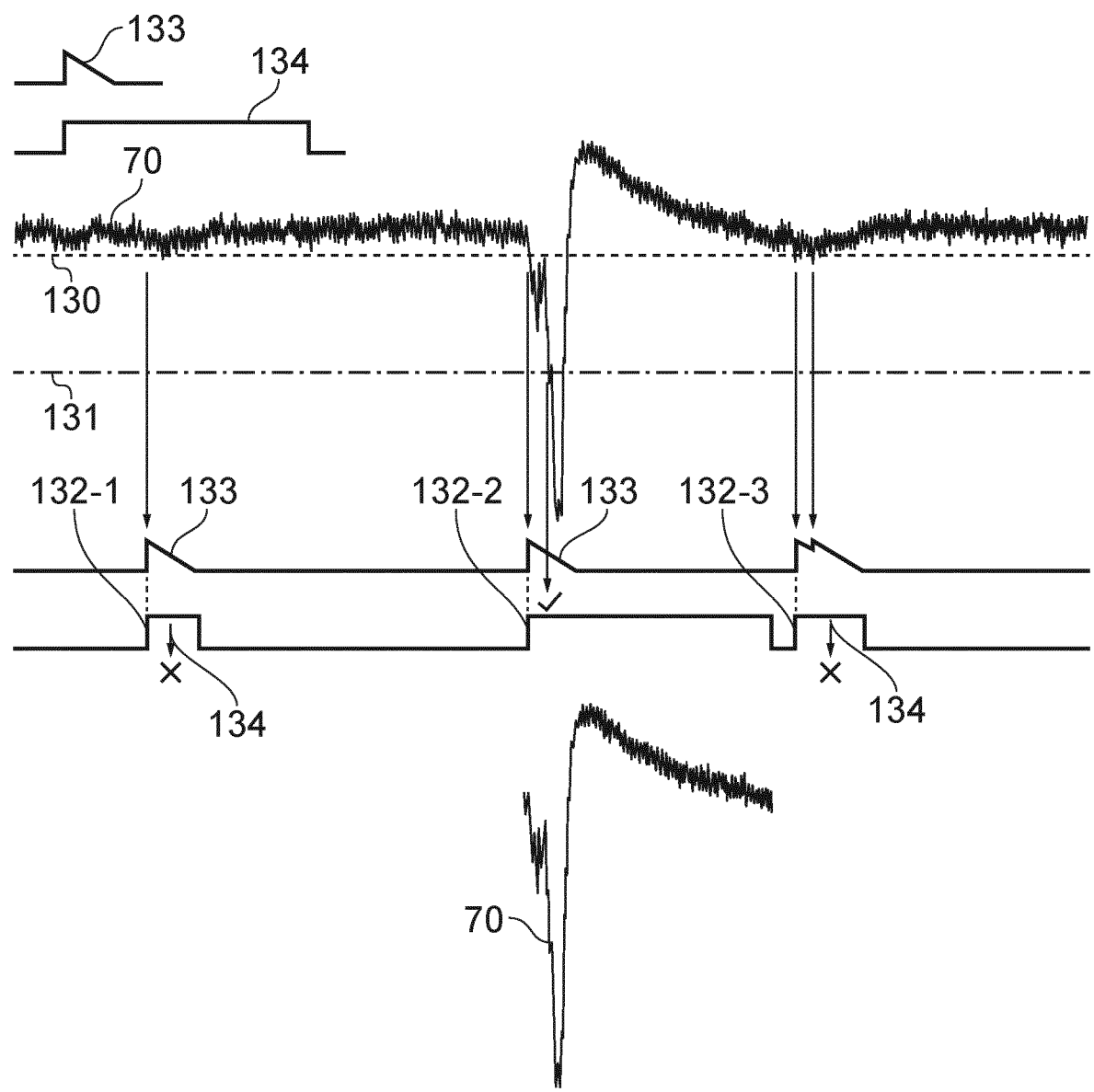
FIG. 13 shows an example of activity detection from an electrode signal together with sampling window signals and sampling window counter signals as triggered by lower and upper threshold signals.

FIG. 13 illustrates another activity sensing strategy in which the timing and duration of the sampling window 134 can be automatically varied according to properties of the electrode signal 70. Two different thresholds, a lower threshold 130 and an upper threshold 131 may be generated by a DAC associated with an electrode, e.g. a DAC that is specific to the individual electrode or shared by a plurality of electrodes. The lower threshold defines a pre-activation of the window when the sampling starts, e.g. the sampling starts at 132-1, 132-2, 132-3 as seen in FIG. 13 when the electrode signal reaches the lower threshold. When the lower threshold is reached, the samples are stored in a buffer (e.g. buffer 61), but the sampling window 134 is only continued and samples are only stored for further read out/upload if the electrode signal reaches the upper threshold 131 within a programmable time interval of the lower threshold crossing. The programmable time window is defined by a counter 133. If the electrode signal does not reach the upper threshold 131 before the counter 133 times out, the samples that have been buffered for that window are discarded, e.g. not streamed/uploaded from the buffer to the external data sink 11 by the streaming sequencer 66. This allows the initial waveform of an activation signal to be acquired that would normally not be sampled until the upper threshold 131 is reached, thereby obtaining more potentially useful signal data for genuine signal events without unduly increasing the number of non-relevant samples or susceptibility of a system to oversampling due to noise.

Other more complex sampling protocols for defining variable sampling window lengths can be defined, such as increased numbers and types of thresholds. Other signal properties may also be used for detecting thresholds, to define other complex sampling protocols. These may also be implemented using multiple activity flags for each electrode.

Figure 10A:
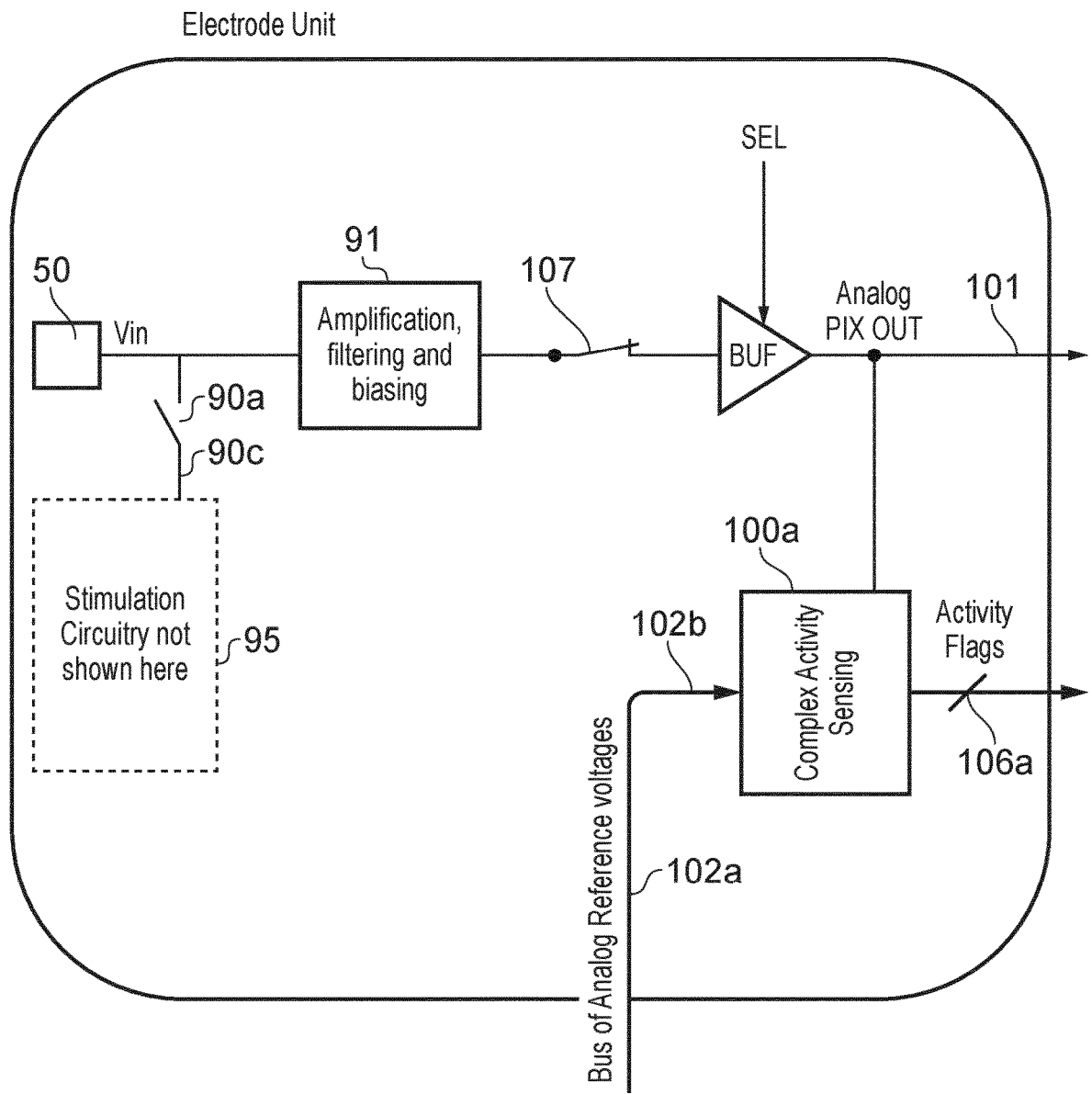
FIG. 10A shows an alternative, generalised complex electrode activity sensor arrangement.

With reference to FIG. 10A, an alternative circuit to that of FIG. 10 and suitable for use as an electrode activity sensor arrangement has a functionally more complex activity sensor and range sensor 100a. Instead of the comparator 105 and synchronized DC voltage ramp 102 of FIG. 10, the activity detector 100a of FIG. 10A enables signal sampling through activity flags 106a generalized in a bus of several bits, based on a set of different voltage references 102a on multiple signal lines 102b, where each one can contain different voltage levels, arranged in a ramp-sequence. The acquisition sequencer 65 synchronizes and triggers the various DACs needed to generate the appropriate voltage levels/thresholds at a given time. Hence, it is possible with such a configuration (i.e. multiple analogue thresholds, multiple activity flags) to generate complex activity conditions to gate signal sampling (such as the examples of FIGS. 12 and 13). Additionally, programmable logic can be implemented in the acquisition sequencer 65 to dynamically perform gating adapted to changing statistical distributions of the signal.

The apparatus described above enables the highly efficient reduction of the amount of transmitted data necessary by sampling data only according to activated electrodes and avoiding sampling overhead in respect of portions of electrode signals that do not carry relevant information. This enables the keeping of important information such as waveforms and need not only focus on specific events (e.g. spikes). Power consumption may be reduced by switching off amplifiers and ADCs when they are not required for sampling. The performance of the active electrodes may be improved, e.g. by increasing the individual electrode's current budgets to improve noise performance or gain as a result of the saving of sampling overhead.

The efficiency of the activity detector can depend on the type of waveforms and biological models that need to be recorded and of the applied detection conditions. Electrode signals from a primary culture can substantially differ in nature from the type of signals recorded from acute brain slices. Any activity detection that occurs prior to, and which triggers, sampling (as shown in FIG. 10A) is not able to capture signals that occur before the detection criteria are met. However, sometimes it is desirable to also capture a signal waveform or register information from an electrode signal that occurs before the actual activity event. The starting phase of neural signals which are not strong enough to trigger the activity detector, is an example thereof.

Figure 10B:
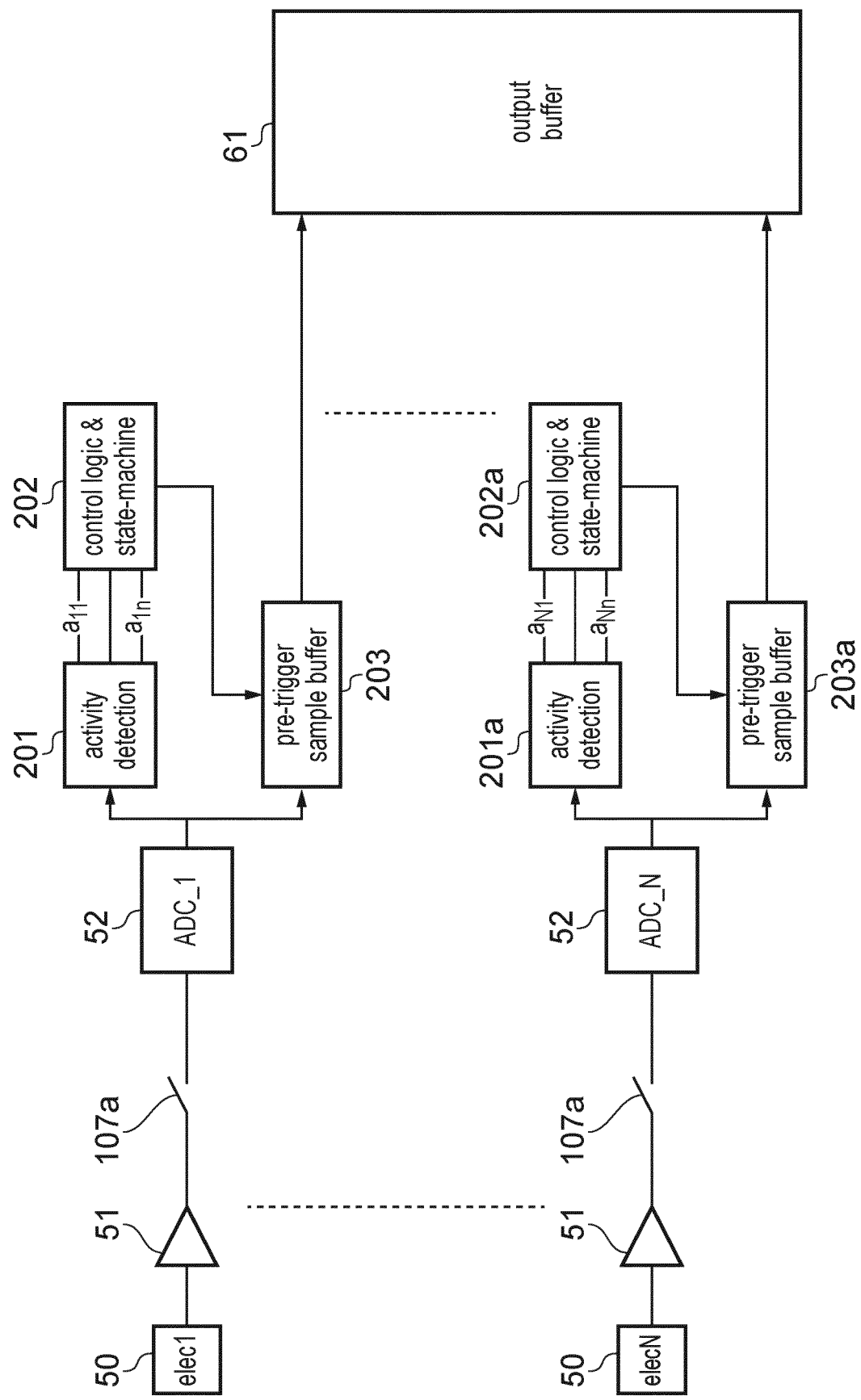
FIG. 10B shows a sampling circuit arrangement in which analogue-to-digital conversion occurs prior to activity detection such that activity detection is performed on digitized data and a cyclic buffer is used for each electrode to store a most recent course of the signal prior to activity detection.

In this context, the microelectrode array may be implemented using, for example, an arrangement such as shown in FIG. 10B. FIG. 10B shows electrodes 50, as previously described, where each is coupled to a respective amplifier 51 and ADC 52 as a sampling circuit. The output of each ADC 52 is coupled to a respective activity sensor 201 and to a pre-trigger sample buffer 203. A control logic module 202 receives input from the activity sensor 201 and controls operation of the pre-trigger sample buffer 203 and downstream sample buffer 61. Similar to the arrangement of FIG. 10, switches 107a may be used to disconnect the outputs of the amplifiers 51 when an electrode is in stimulation mode.

In the example of FIG. 10B, the ADCs 52 each associated with a respective electrode 50 may operate continuously or effectively continuously, performing analogue-to-digital conversion to sample the electrode signal on the electrode 50 and the sampled values are stored in the pre-activation sample buffer ("pre-trigger buffer") 203. The pre-trigger buffer memory is generally referred to herein as a cyclic buffer such as a ring buffer or first-in-first-out (FIFO) buffer, in which streamed samples from the associated ADC are stored for a predetermined period of time and then overwritten in time sequence with new samples after the predetermined period of time (e.g. when the cyclic buffer is full). If the activity sensor 201 detects an electrode signal event above a threshold and as defined above, e.g. achievement of a set of conditions required to set an activity flag, not only can all samples taken while the activity flag is set be gated to the sample buffer 61 as described earlier, but in addition the sample or samples already stored in the cyclic buffer 203 representative of the electrode signal just prior to setting of the activity flag can also be gated to the sample buffer 61. It will be recognised that the duration of the pre-activation window, i.e. the duration of waveform or samples captured and retained in the cyclic buffer 203 before detection of an electrode signal event, can be chosen by provision of a cyclic buffer of appropriate length or capacity.

It is also possible to provide a sampling circuit which provides the cyclic buffer arrangement of FIG. 10B for only a selected subset of electrodes 50, with other electrodes having a sampling circuit and/or activity sensor arrangement such as exemplified in FIGS. 5, 6, 10 and 10A. In a further arrangement, a plurality of electrodes 50 may share a cyclic buffer 203, e.g. with samples from each ADC being interleaved.

It will also be recognised that an arrangement exemplified by FIG. 10B enables the activity detection to occur in the digital domain, i.e. after sampling by the ADC. This may allow a more complex set of conditions, or more complex logic, to be applied to determine whether an electrode signal event above a predetermined threshold has occurred. Instead, or in addition, activity sensing could still be performed in the analogue domain if the activity sensor 201 is coupled to the output of amplifier 51, while the cyclic buffer 203 still buffers pre-trigger samples from the ADC 52.

Control logic may be configured to determine an activity duration for a particular detected event or for types of detected electrode events. The measured activity duration might then be used to dynamically adapt a window duration for maintaining an activity flag for that event or type of event and/or to determine a length of the pre-trigger cyclic buffer used to record events based on the type of event.

The techniques described above provide for multi-well environments for in-vitro applications, with large number of MEA chips and reduced interconnection requirements per sensor. The MEA chips are networked, and consist of sensing and actuating ASICs and computational nodes for complex and smart interaction with biological systems, to efficiently handle large amount of sparse data. The techniques described above also provide for single or multi-MEA environment for in-vivo applications, e.g. requiring low power consumption and low interconnection density.

The described devices/systems can be typically used in the following fields: (i) neuro-scientific research to perform functional studies on the connectivity, physiology and pathology of brain assemblies; (ii) industrial pharmaceutical screenings for safety, toxicology, and identification of effect and mechanism of action of potentially neuro-protective or neuro-toxic compounds; (iii) in vivo applications in human disease requiring very low power devices for use with batteries and low interconnection MEAs to decouple the MEA probe, which is in contact with the brain, from the skull (untethered design).

Figure 11:
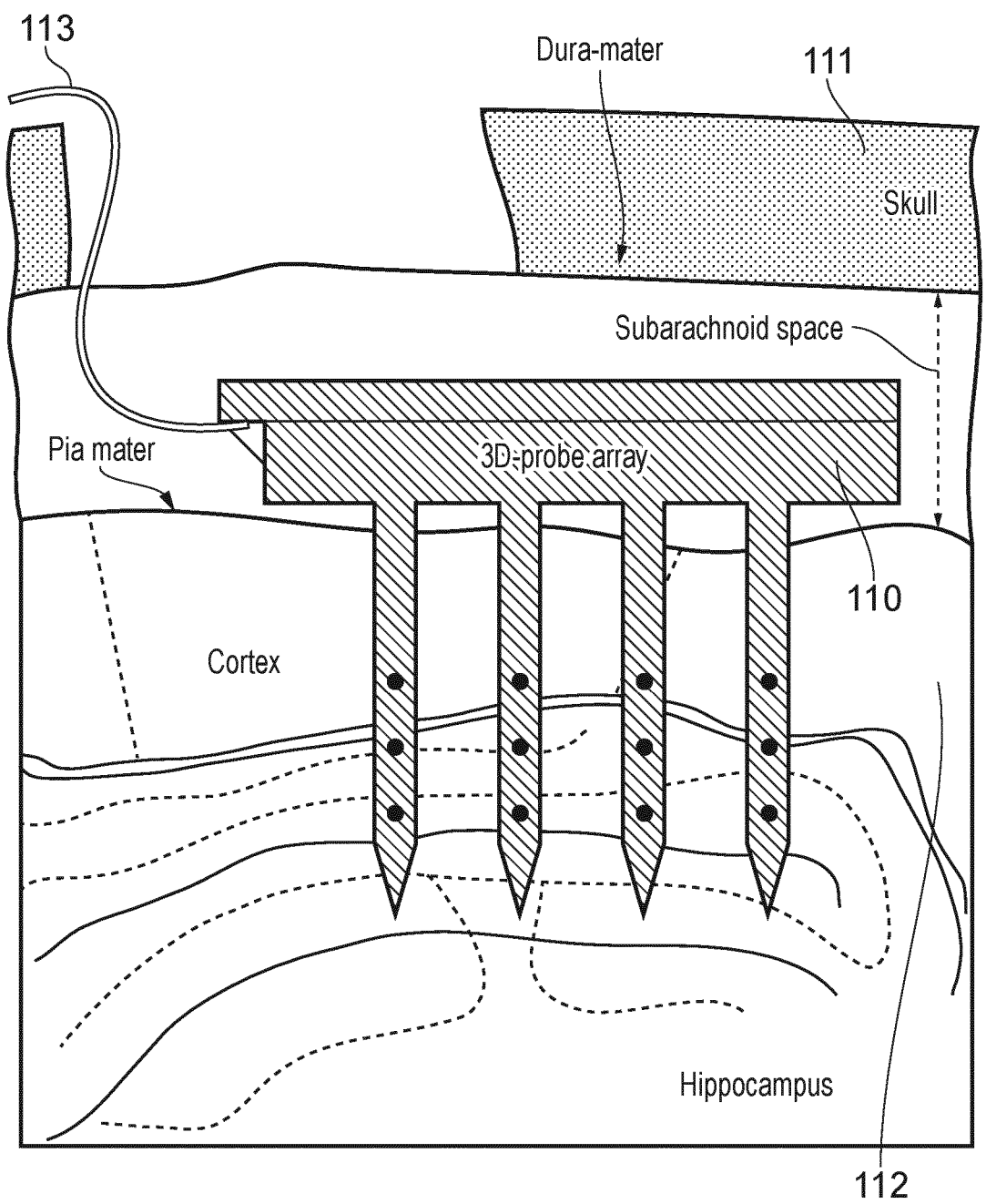
FIG. 11 shows a diagram illustrating a context of use of a probe array.

An example of the third application above is illustrated in FIG. 11 (from Kim S et al, Microdevices 11, 453-456). A probe array 110 anchored or in some way too much tied to the skull 111 may cause injuries to the brain tissue because of the relative motion between the skull and the brain 112 and has the potential to be dislodged from its position. In the example of FIG. 11, the wiring 113 extending from the probe array 110 should be as thin and as flexible as possible, e.g. incorporating as few wires as possible. The strategic sampling arrangements described above enable a substantial reduction in the quantity of data that must be transmitted to and/or from the array and therefore can significantly contribute to a reduction in the hardware specification of the wiring 113.

The devices described herein are suitable for any kind of electrogenic cells, i.e. cells exhibiting electrical activity such as neurons, cardiac cell, muscular cells, pancreatic cells. Particularly beneficial applications may comprise use with neuronal cells and cardiac cells.

The networked arrangements and/or activity-based sampling features as described above may advantageously be used to enable the placement of sensors in the cortex to create complete human-machine interfaces or enable the provision of high-throughput devices for pharma-screening that will require the integration of many MEA sensors on a single circuit board substrate, e.g. where each sample well needs a sensor. In existing products with low numbers of MEAs (e.g. six-well screening arrangements), currently techniques route each sensor output (analog or digital) to a centralized computational unit (e.g. FPGA). This strategy is not sustainable for dozens or hundreds of sensors, and the use of activity sensing and/or the networking of MEAs with shared buses and placement of computational nodes for each or groups of MEAs in a network can significantly increase the number of MEAs that can be manged within a single system.

The techniques described above may be implemented using microelectrode arrays formed by using flexible multi-electrode polymer probes, e.g. using thin film materials, that integrate one or multiple electrodes per probe and that are interfaced with an application-specific integrated circuit (ASIC) to implement signal amplification stages etc.

Other embodiments are intentionally within the scope of the accompanying claims.

The invention claimed is:

1. A microelectrode array for obtaining electrical signals from electrogenic cell material, comprising:
   an array of electrodes, each electrode having associated with it a sampling circuit for sampling an electrode signal on the electrode, and a sample buffer to store a representation of the electrode signal from the electrode, each electrode further having associated with it an activity sensor configured to detect at least one electrode signal event above a predetermined threshold and to set at least one activity flag based on the detection;

the microelectrode array further comprising control logic to activate the sampling circuit and sample buffer of an electrode to sample the electrode signal and store a representation of the sampled electrode signal comprising plural samples of the electrode signal for that electrode only when the activity flag is set, wherein said control logic is configured to determine a duration of a sampling window based on the at least one activity flag and that follows the detected event, the duration comprising a period sufficient to capture said plural samples from the electrode.

2. A microelectrode array for obtaining electrical signals from electrogenic cell material, comprising:

an array of electrodes, each electrode (50) having associated with it a sampling circuit (51, 52) for sampling an electrode signal on the electrode, a cyclic buffer (203) receiving the sampled electrode signals from the sampling circuit and a sample buffer (61) to store a representation of the electrode signal from the cyclic buffer, each electrode further having associated with it an activity sensor (201) configured to detect at least one electrode signal event above a predetermined threshold and to set at least one activity flag based on the detection;

the microelectrode array further comprising control logic (202) to gate data from the cyclic buffer (203) of an electrode to the sample buffer (61) to store a representation of the sampled electrode signal representative of plural samples for that electrode only when the activity flag is set, wherein said control logic is configured to determine a duration, based on the activity flag, sufficient to gate the data representative of the plural samples from the electrode following the detected event, wherein the control logic determines, in effect, the duration of a sampling window during which the plural samples are captured.

3. The microelectrode array of claim 2, wherein:

the sampling circuit includes, for each electrode, an ADC configured to convert the electrode signal on the electrode to a digital form and transfer the sampled electrode signal to the cyclic buffer, and the activity sensor is configured to detect the electrode signal events above a predetermined threshold based on the electrode signal in digital form from the ADC, and wherein the control logic is configured to gate the data in digital form from the cyclic buffer (203) to the sample buffer (61) to store the representation of the sampled electrode signal representative of plural samples in digital form.

4. A multi-microelectrode array comprising a plurality of microelectrode arrays according to claim 2 arranged in a network, each microelectrode array including a status register indicating a status of at least one sample buffer of the array, and further comprising:

a network controller, coupled to each microelectrode array by a bus, the network controller being configured to schedule transmission of sample buffer contents of the plurality of microelectrode arrays over the bus according to the condition of the respective status registers.

5. The multi-microelectrode array of claim 4, in which one of:

the plurality of microelectrode arrays are arranged in a tree network comprising a root node coupled by a control channel line to each of a plurality of parent nodes, each parent node being coupled by a further control channel line to each of a plurality of respective child nodes, the network controller being configured to schedule the transmission of sample buffer contents of the plurality of microelectrode arrays, over the bus, using a hierarchy of control lines; and the plurality of microelectrode arrays are arranged in parallel sub-groups, each sub-group having a said bus and a common control channel line, the network controller being configured to schedule the transmission of sample buffer contents of the plurality microelectrode arrays in each respective group, over the respective bus, using the respective common control channel line for that group.

6. The microelectrode array of claim 2, in which each sampling circuit comprises an analogue-to-digital converter (ADC) and the control logic is configured to switch the respective ADC for an electrode from a quiescent state to an active state when a respective activity flag is set and to return the respective ADC from the active state to a quiescent state when any respective activity flags are not set.

7. The microelectrode array of claim 2, in which the control logic is further configured to tag each sample stored in the sample buffer with an identification of the electrode from which the sample was taken and/or a time indication associated with the sample.

8. The microelectrode array of claim 1, in which one of:
each activity sensor is shared by a plurality of electrodes; or
each electrode has its own activity sensor separate from activity sensors for other electrodes.

9. The microelectrode array of claim 1, in which each sampling circuit comprises an analogue-to-digital converter (ADC) and the control logic is configured to switch the respective ADC for an electrode from a quiescent state to an active state when a respective activity flag is set and to return the respective ADC from the active state to a quiescent state when any respective activity flags are not set.

10. The microelectrode array of claim 9, in which the or each sample buffer is coupled to a data bus for transmitting stored samples to a receiver together with respective sample tags.

11. The microelectrode array of claim 1, in which the control logic is further configured to tag each sample stored in the sample buffer with an identification of the electrode from which the sample was taken and/or a time indication associated with the sample.

12. The microelectrode array of claim 1, wherein the duration of the sampling window is programmable.

13. The microelectrode array of claim 1, in which the activity flag remains set for a period of between 2 and 200 ms or between 10 and 500 ms following detection of an electrode signal event.

14. The microelectrode array of claim 12, in which the control logic is further configured to determine an activity type based on a detected event and to adapt the duration of sampling window based on the activity type.

15. The microelectrode array of claim 1, in which the control logic is further configured to determine an activity type based on a detected event and to adapt a threshold level required to detect an event based on the activity type.

16. The microelectrode array of claim 1, in which the duration of the sampling window has a variable length based on at least one property of the electrode signal.

17. The microelectrode array of claim 1, further configured such that, when an activity flag is set for one or more electrodes for which an electrode signal event above a predetermined threshold has been detected, activity flags are automatically set for one or more adjacent electrodes in a predetermined region of attention.

18. The microelectrode array of claim 1, in which each electrode further includes a range sensor configured to detect a measure of signal amplitude associated with each detected event and to set a range flag based thereon, and in which the control logic is configured to adjust a gain of the sampling circuit based on the range flag.

19. The microelectrode array of claim 1, in which each activity sensor is configured to perform the detection of a signal event based on any one or more of amplitude, spectral content and energy of the respective electrode signal event.

20. The microelectrode array of claim 1, in which the or each sampling circuit is shared by a plurality of electrodes and the control logic is further configured to sequence access to the shared sampling circuit and/or shared sample buffer by each of the plurality of electrodes for which the respective activity flag is set.

21. The microelectrode array of claim 1, in which each electrode further includes stimulation circuitry for applying a stimulation signal to the electrode at times when the activity sensing is disabled.

22. The microelectrode array of claim 1, in which each activity sensor is configured to set the activity flag based on the electrode signal relationship to multiple thresholds.

* * * * *